United States Patent
Wilson et al.

(10) Patent No.: US 10,988,533 B2
(45) Date of Patent: Apr. 27, 2021

(54) ANTI-PRE-BCR ANTAGONISTS AND METHODS

(71) Applicants: STC.UNM, Albuquerque, NM (US); Bridget S. Wilson, Albuquerque, NM (US); Stuart S. Winter, Albuquerque, NM (US); Michael Frank Erasmus, Santa Fe, NM (US); Michael Horowitz, Los Altos, CA (US)

(72) Inventors: Bridget S. Wilson, Albuquerque, NM (US); Stuart S. Winter, Albuquerque, NM (US); Michael Frank Erasmus, Santa Fe, NM (US); Michael Horowitz, Los Altos, CA (US)

(73) Assignees: UNM Rainforest Innovations, Albuquerque, NM (US); Michael Horowitz, Los Altos, CA (US)

( * ) Notice: Subject to any disclaimer, the term of this patent is extended or adjusted under 35 U.S.C. 154(b) by 0 days.

(21) Appl. No.: 15/548,871

(22) PCT Filed: Feb. 5, 2016

(86) PCT No.: PCT/US2016/016753
§ 371 (c)(1),
(2) Date: Aug. 4, 2017

(87) PCT Pub. No.: WO2016/127043
PCT Pub. Date: Aug. 11, 2016

(65) Prior Publication Data
US 2018/0022805 A1   Jan. 25, 2018

Related U.S. Application Data

(60) Provisional application No. 62/112,339, filed on Feb. 5, 2015.

(51) Int. Cl.
*A61K 39/395* (2006.01)
*C07K 16/28* (2006.01)
*A61P 35/02* (2006.01)

(52) U.S. Cl.
CPC ...... *C07K 16/2803* (2013.01); *A61K 39/3955* (2013.01); *A61P 35/02* (2018.01); *C07K 2317/21* (2013.01); *C07K 2317/24* (2013.01); *C07K 2317/35* (2013.01); *C07K 2317/52* (2013.01); *C07K 2317/55* (2013.01); *C07K 2317/622* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,335,157 B1 | 1/2002 | Tsuganezawa et al. | |
| 6,335,175 B1 * | 1/2002 | Tsuganezawa et al. | ................... C07K 16/28 424/130.1 |
| 2003/0215453 A1 | 11/2003 | Dedra et al. | |
| 2011/0262440 A1 | 10/2011 | Zugmaier | |
| 2014/0228544 A1 | 8/2014 | Bhatt et al. | |
| 2016/0009813 A1 * | 1/2016 | Themeli et al. | ... A61K 39/0011 424/134.1 |

FOREIGN PATENT DOCUMENTS

| | | |
|---|---|---|
| JP | H1142087 A | 2/1999 |
| JP | H11133028 A | 5/1999 |
| WO | WO 2004/106381 A1 | 12/2004 |
| WO | WO 2016/126488 A1 | 8/2016 |
| WO | WO 2016/127043 A1 | 8/2016 |

OTHER PUBLICATIONS

Van der Veer et al.,"Interference with pre-B-cell receptor signaling offers a therapeutic option for TCF3-rearranged childhood acute lymphoblastic leukemia", Blood Cancer Journal 4, e181, pp. 1-4 (Year: 2014).*
Owens et al 1994 J of Immunolog. Method 1994, v.168-149-165.*
International Search Report and Written Opinion: PCT/US2016/016753, filed May 26, 2016, 9 pgs.
Notice of International Preliminary Report on Patentability: PCT/US2016/016753, filed Aug. 17, 2017, 8 pgs.
Safdari of al., "Antibody humanization methods—a review and update," 2013, *Biotechnology and Genetic Engineering Reviews*, vol. 29(2); pp. 175-186.
Andrews et al., "Actin restricts FcεRI diffusion and facilitates antigen-induced receptor immobilization," *Nat Cell biology*, Aug. 2008; 10:955-963.
Andrews et al., "Small, Mobile FcεRI Receptor Aggregates are Signaling Competent," *Immunity*, Sep. 18, 2009; 31:469-479.
Asner et al., "Obesity in Long-Term Survivors of Childhood Acute Lymphoblastic Leukemia," *Pediatric Blood Cancer*, 2008; 51:118-122.
Babor et al., "Invasive Aspergillosis in Pediatric Oncology Patients: A Rare Event with Poor Prognosis—Case Analysis to Plan Better Targeted Prophylactic or Therapeutic Measurement," *Klin Padiatr*, 2012; 224:160-165.

(Continued)

*Primary Examiner* — Michail A Belyavskyi
(74) *Attorney, Agent, or Firm* — Mueting Raasch Group

(57) ABSTRACT

This disclosure describes the identification of pre-B Cell Receptor (pre-BCR) antagonists and the use of pre-BCR antagonists as a targeted therapy. The compositions and methods generally involve a composition that includes a pre-B cell receptor (pre-BCR) antagonist and is engineered for expression as a T cell chimeric receptor. In some embodiments, the pre-BCR antagonists can include an anti-pre-BCR antibody.

7 Claims, 27 Drawing Sheets

Specification includes a Sequence Listing.

(56) References Cited

OTHER PUBLICATIONS

Bankovich et al., "Structural Insight into Pre-B Cell Receptor Function," *Science*, Apr. 13, 2007; 316:291-294.
Barondes et al., "Structure and Function of a Large Family of Animal Lectins," *The Journal of Biological Chemistry*, Aug. 19, 1994; 269(33):20807-20810.
Bologa et al. "Compound Collection Preparation for Virtual Screening," *Methods in Molecular Biology*, 2012; 910:125-143.
Bradbury et al., "Beyond natural antibodies: the power of in vitro display technologies," *Nature Biotechnology*, Mar. 2011; vol. 29(3):245-254.
Cardo-Vila et al., "From combinatorial peptide selection to drug prototype (II): Targeting the epidermal growth factor receptor pathway," *PNAS*, Mar. 16, 2010; 107(11): 5118-5123.
Carroll-Portillo et al., "Formation of a Mast Cell Synapse: FcεRI Membrane Dynamics upon Binding Mobile or Immobilized Ligands on Surfaces," *J. of Immunology*, 2010; 184: 1328-1338.
Cutler et al., "Multi-Color Quantum Dot Tracking Using a High-Speed Hyperspectral Line-Scanning Microscope," *Plos One*, May 2013; 8(5): e64320.
Davis et al., "Chronic active B-cell-receptor signaling in diffuse large B-cell lymphoma," *Nature*, Jan. 7, 2010; 463:88-92.
Douer, "Adult Acute Lymphoblastic Leukemia: A Cancer with No Standard of Care," *Acta Haematol*, Apr. 2013; 130:196-198.
Elantak et al., "Structural Basis for Galectin-1-dependent Pre-B cell Receptor (Pre-BCR) Activation," *The Journal of Biological Chemistry*, 2012; 287(53):44703-44713.
Eswar et al., "Comparative Protein Structure Modeling Using Modeller," *Curr Protoc Bioinformatics*, Oct. 2006, Unit-5.6, 47 pages.
Ferrara et al., "Using Phage and Yeast Display to Select Hundreds of Monoclonal Antibodies: Application to Antigen 85, a Tuberculosis Biomarker," *Plos One*, Nov. 2012; 7(11): e49535.
Gauthier et al., "Galectin-1 is a stromal cell ligand of the pre-B cell receptor (BCR) implicated in synapse formation between pre-B and stromal cells and in pre-BCR triggering," *PNAS*, Oct. 1, 2002; 99(20):13014-13019.
Gaynon et al., "Long-term Results of the Children's Cancer Group Studies for Childhood Acute Lymphoblastic Leukemia 1983-2002: a Children's Oncology Group Report," *Leukemia*, Feb. 2010; 24(2):285-297.
Giordano et al., "Galectins in hematological malignancies" *Current Opinion in Hematology*, 2013; 20:327-335.
Goennenwein et al., "Functional Incorporation of Integrins into Solid Supported Membranes on Ultrathin Films of Cellulose: Impact on Adhesion," *Biophysical Journal*, Jul. 2003; 85:646-655.
Harvey et al., "Identification of novel cluster groups in pediatric high-risk B-precursor acute lymphoblastic leukemia with gene expression profiling: correlation with genome-wide DNA copy number alterations, clinical characteristics, and outcome," *Blood*, Dec. 2, 2010; vol. 116(23): 4874-4884.
Hauser et al., "Calmodulin inhibition of E2A stops expression of surrogate light chains of the pre-B-cell receptor and CD19," *Molecular Immunology*, 2010; 47:1031-1038.
Hunger et al., "Improving Outcomes for High-Risk ALL: Translating New Discoveries Into Clinical Care" *Pediatric Blood & Cancer*, 2011; vol. 56:984-993.
Hunger et al., "Childhood Leukemia—New Advances and Challenges," *New England J. Of Medicine*, Aug. 5, 2004; 351(6): 601-603.
Karasuyama et al., "A Complex of Glycoproteins Is Associated with VpreBλ5 Surrogate Light Chain on the Surface of μ Heavy Chain-negative Early Precursor B Cell Lines," *J Exp. Med*, The Rockefeller University Press, Aug. 1993; 178:469-478.
Kepley et al., "Negative regulation of FcεRI signaling by FcγRII costimulation in human blood basophils" *J. Allergy Clinical Immunology*, 2000; 106(2):337-348.

Kim et al., "Independent Trafficking of Ig-χIg-β and μ— Heavy Chain Is Facilitatied by Dissociation of the B Cell Antigen Receptor Complex," *J. Immunology*, 2005; 175:147-154.
Kiyokawa et al., "Diagnostic importance of CD170a/b as markers of precursor B-cell lymphoblastic lymphoma," *Modern Pathology*, 2004; 17:423-429.
Lemmers et al. "The Human (ψL+μ–) proB Complex: Cell Surface Expression and Biochemical Structure of a Putative Transducing Receptor," *Blood*, Jun. 15, 1999; 93(12):4336-4346.
Lidke et al., "Quantun dot ligands provide new insights into erB/HER receptor-mediated signal transduction" *Nature Biotechnology*, Feb. 2004; 22(2): 198-203.
Lidke et al., "Caught in the act: quantifying protein behavior in living cells," *Trends in Cell Biology*, 2004; 19(11):566-573.
Lillemeier et al., "Plasma membrane-associated proteins are clustered into islands attached to the cytoskeleton" *PNAS*, Dec. 12, 2006; 103(50):18992-18997.
Low-Nam et al., "ErbB1 dimerization is promoted by domain co-confinement and stabilized by ligand binding," *Nature Structural & Molecular Biology*, Nov. 2011; vol. 18(11):1244-1249.
Lund et al., "Risk Factors for Treatment Related Mortality in Childhood Acute Lymphoblastic Leukaemia," *Pediatric Blood & Cancer*, 2011; 56:551-559.
Matlawska-Wasowska et al, "Macrophage and NK-mediated Killing of Precursor-B Acute Lymphoblastic Leukemia Cells Targeted with a-Fucosylated Anti-CD19 Humanized Antibodies," *Leukemia*, Jun. 2013; 27(6):1263-1274.
Meng et al., "IKK inhibitor bay 11-7082 induces necroptotic cell death in precursor-B acute lymphoblastic leukaemic blasts" *British J. Haematology*, 2010; 148:487-490.
Meng et al., "GSI-I (Z-LLNle-DHO) inhibits γ-secretase and the proteasome trigger cell death in precursor-B acute lymphoblastic leukemia" *Leukemia*, 2011; 25:1135-1146.
Monroe, "ITAM-mediated tonic signaling through pre-BCR and BCR complexes," *Nature Reviews. Immunology*, Apr. 2006; 6:283-294.
Mourcin et al., "Galectin-1-expressing stromal cells constitute a specific niche for pre-B11 cell development in mouse bone marrow," *Blood*, Jun. 16, 2011; 117(24):6552-6561.
Niemann et al., "B-cell receptor signaling as a driver of lymphoma development and evolution,", *Seminars in Cancer Biology*, Dec. 2013; 23:410-421.
Ohnishi et al., "The nonimmunoglobulin portion of λ5 mediates cell-autonomous pre-B cell receptor signaling," *Nature Immunology*, Sep. 2003; 4(9): 849-856.
Oliver et al., "Inhibition of Mast Cell FcεR1-mediated Signaling and Effector Function by the Syk-selective Inhibitor, Piceatannol," *The J.of Biological Chemistry*, Nov. 25, 1994; 269(47):29697-29703.
Oprea et al., "Integrating virtual screening in lead discovery," *Current Opinion in Chemical Biology*, 2004; 8:349-358.
Oprea et al., "Drug repuoposing from an academic perspective," *Drug Discovery Today: Therapeutic Strategies*, 2011; 8(3-4): 61-69.
Peluso et al., "Optimizing antibody immobilization strategies for the construction of protein microarrays," *Analytical Biochemistry*, 2003; 312:113-124.
Rossi et al., "Clustering of Pre-B Cell Integrins Induces Gelactin-1-Dependent Pre-B Cell Receptor Relocalization and Activation," *Journal of Immunology*, 2006; 177: 796-803.
Russell et al., "Differential Expression of Ikaros Isoforms in Monozygotic Twins With MLL-rearranged Precursor-B Acute Lymphoblastic Leukemia," *Journal of Pediatric Hematology/Oncology*, Dec. 2008; 30(12):941-944.
Shen et al., "Statistical potential for assessment and prediction of protein structures," *Protein Science: a publication of the Protein Society*, 2006; 15:2507-2524.
Steinkamp et al., "erbB3 Is an Active Tyrosine Kinase Capable of Homo- and Heterointeractions," *Molecular and Cellular Biology*, Mar. 2014; 34(6):965-977.
Stevenson et al., "B-cell receptor signaling in chronic lymphocytic leukemia," *Blood*, Oct. 20, 2011; 118(16):4313-4320.
Tovchigrechko et al., "GRAMM-X public web server for protein-protein docking," *Nucleic Acids Research*, 2006; 34:W310-314.

(56) References Cited

OTHER PUBLICATIONS

Tsourkas et al., "Discrimination of membrane antigen affinity by B Cells requires dominance of kinetic proofreading over serial engagement," *Cellular & Molecular Immunology*, 2012; 9:62-74.
Wayne, "Application of Immunotherapy in Pediatric Leukemia," *Current Hematologic Malignancy Reports*, 2009; 4:159-166.
Wells, "Geometric Simulation of Flexible Motion in Proteins," *Methods in Molecular Biology*, 2014; 1084:173-192.
Wilson et al., "Spatio-temporal Signaling in Mast Cells," *Advances Exp. Med Biol.*, 2011; 716:1-106.
Winnick et al., "Childhood Lukemia—New Advances and Challenges," *The New England Journal of Medicine*, Aug. 5, 2004; 351(6):601-603.
Winter et al., "High-Throughput Screening for Daunorubicin-Mediated Drug Resistance Identifies Mometasone Furoate as a Novel ABCB1-Reversal Agent," *Journal of Biomolecular Screening*, 2008; 13(3):185-193.
Winter et al., "Identification of genomic classifiers that distinguish induction failure in T-lineage acute lymphoblastic leukemia: a report from the Children's Oncology Group," *Blood*, Sep. 1, 2007; 110(5):1429-1438.
Winter, "Pediatric Acute Leukemia Therapies Informed by Molecular Analysis of High-Risk Disease," *American Society of Hematology*, 2011; 366-373.
Extended European Search Report: PCT/US2016/016753, dated Aug. 29, 2018; 8 pages.

\* cited by examiner

A

B

C

D

A

C

A

B

A

B

C

D

E

A

B

E

F

I

J

A

B

C

D

SEQUENCE LISTING

```
<160> NUMBER OF SEQ ID NOS: 13

<210> SEQ ID NO 1
<211> LENGTH: 19
<212> TYPE: PRT
<213> ORGANISM: Artificial
<220> FEATURE:
<223> OTHER INFORMATION: Peptide

<400> SEQUENCE: 1

Met Ser Trp Ala Pro Val Leu Leu Met Leu Phe Val Tyr Cys Thr Gly
1               5                   10                  15

Cys Gly Pro

<210> SEQ ID NO 2
<211> LENGTH: 126
<212> TYPE: PRT
<213> ORGANISM: Artificial
<220> FEATURE:
<223> OTHER INFORMATION: immunoglobulin iota chain

<400> SEQUENCE: 2

Gln Pro Val Leu His Gln Pro Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Glu Lys Glu Glu Arg Glu Arg Glu Trp
            100                 105                 110
```

Glu Glu Glu Met Glu Pro Thr Ala Ala Arg Thr Arg Val Pro
            115                 120                 125

<210> SEQ ID NO 3
<211> LENGTH: 145
<212> TYPE: PRT
<213> ORGANISM: Artificial
<220> FEATURE:
<223> OTHER INFORMATION: immunoglobulin iota chain

<400> SEQUENCE: 3

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Arg Glu
        115                 120                 125

Arg Glu Trp Glu Glu Glu Met Glu Pro Thr Ala Ala Arg Thr Arg Val
    130                 135                 140

Pro
145

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
caccatggct tgtggtctgg                                              20

<210> SEQ ID NO 5
<211> LENGTH: 26
<212> TYPE: DNA
<213> ORGANISM: Artificial
<220> FEATURE:
<223> OTHER INFORMATION: Primer

<400> SEQUENCE: 5
tcagtcaaag gccacacatt tgatct                                       26

<210> SEQ ID NO 6
<211> LENGTH: 88
<212> TYPE: PRT
<213> ORGANISM: Homo Sapiens

<400> SEQUENCE: 6

Asp Ile Gln Leu Thr Gln Ser Pro Ser Phe Leu Ser Ala Ser Val Gly
1               5                   10                  15

```
Asp Arg Val Thr Ile Thr Cys Arg Ala Ser Gln Gly Ile Ser Thr Asp
                20                  25                  30

Leu Asn Trp Tyr Gln Gln Lys Pro Gly Lys Ala Pro Lys Leu Leu Ile
             35                  40                  45

Tyr Ala Ala Ser Asn Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys
                85

<210> SEQ ID NO 7
<211> LENGTH: 6
<212> TYPE: PRT
<213> ORGANISM: Homo Sapiens

<400> SEQUENCE: 7

Gln Gly Ile Ser Thr Asp
1               5

<210> SEQ ID NO 8
<211> LENGTH: 4
<212> TYPE: PRT
<213> ORGANISM: Homo Sapiens
<220> FEATURE:
<221> NAME/KEY: MISC_FEATURE
<222> LOCATION: (4)..(4)
<223> OTHER INFORMATION: This region may include no residues or any
      amino acid.

<400> SEQUENCE: 8

Ala Ala Ser Xaa
1

<210> SEQ ID NO 9
<211> LENGTH: 9
<212> TYPE: PRT
<213> ORGANISM: Homo Sapiens

<400> SEQUENCE: 9

Gln Gln Ser Tyr Asn Trp Pro Tyr Thr
1               5

<210> SEQ ID NO 10
<211> LENGTH: 96
<212> TYPE: PRT
<213> ORGANISM: Homo Sapiens

<400> SEQUENCE: 10

Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Asn Phe
             20                  25                  30

Glu Met Asn Trp Val Arg Gln Ala Pro Gly Lys Gly Leu Glu Trp Val
             35                  40                  45

Ser Gly Ile Ser Ser Asn Gly Arg Tyr Ile Asn Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
<210> SEQ ID NO 11
<211> LENGTH: 8
<212> TYPE: PRT
<213> ORGANISM: Homo Sapiens

<400> SEQUENCE: 11

Gly Phe Thr Phe Ser Asn Phe Glu
1               5

<210> SEQ ID NO 12
<211> LENGTH: 8
<212> TYPE: PRT
<213> ORGANISM: Homo Sapiens

<400> SEQUENCE: 12

Ile Ser Ser Asn Gly Arg Tyr Ile
1               5

<210> SEQ ID NO 13
<211> LENGTH: 15
<212> TYPE: PRT
<213> ORGANISM: Homo Sapiens

<400> SEQUENCE: 13

Ala Arg Val Val Asp Phe Asp Gln Asp Tyr Asn Gly Phe Asp Tyr
1               5                   10                  15
```

ANTI-PRE-BCR ANTAGONISTS AND METHODS

CROSS-REFERENCE TO RELATED APPLICATION

This application is the § 371 U.S. National Stage of International Application No. PCT/US2016/016753, filed Feb. 5, 2016, which claims priority to U.S. Provisional Patent Application Ser. No. 62/112,339, filed Feb. 5, 2015, each of which is incorporated herein by reference.

SEQUENCE LISTING

This application contains a Sequence Listing electronically submitted to the United States Patent and Trademark Office via EFS-Web as an ASCII text file entitled "2019-08-29-SequenceListing_ST25.txt" having a size of 5.88 KB and created on Aug. 29, 2019. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, a composition that includes an antagonist directed at the pre-B cell receptor (pre-BCR).

In some embodiments, the antagonist can be derived from an antibody that specifically binds to a surrogate light component (VpreB, λ5) of the pre-BCR.

In some embodiments, the antibody can include a monovalent antibody fragment such as, for example, a scFv or Fab-Fc. In some embodiments, the antibody can be recombinant and/or engineered to deliver a toxin payload. In some embodiments, the antibody can be humanized. In some embodiments, the antibody can include an anti-VpreB antibody such as, for example, an anti-VpreB1 antibody.

In some embodiments, the antagonist directed at the pre-BCR can include an antibody fragment that is engineered for expression as a T cell chimeric receptor.

In some embodiments, the antagonist directed at the pre-BCR can include a peptide or antibody derivative that blocks pre-BCR binding to galectin, whether soluble or presented in the context of stromal cells.

In another aspect, this disclosure describes a pharmaceutical composition that includes any embodiment of the composition summarized above and a pharmaceutically acceptable carrier.

In another aspect, this disclosure describes a method of treating B cell precursor acute lymphoblastic leukemia (BCP-ALL). Generally, the method includes administering to a subject having BCP-ALL any embodiment of the pharmaceutical composition summarized above in an amount effective to ameliorate at least one symptom or clinical sign of BCP-ALL.

In another aspect, this disclosure describes kits that include any embodiments of the composition summarized above.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

B Cell Precursor Acute Lymphoblastic Leukemia (BCP-ALL) is a common neoplasm in children and is an aggressive disease in adolescents and young adults. Overall survival for BCP-ALL has gradually improved from 10% in the 1960s to approximately 90% presently. Select subsets of patients, however, appear to have not benefited from risk-adapted, intensified therapies, calling for completely novel therapeutic approaches. Because outcomes for high-risk leukemias appear to have plateaued with conventional therapy, the need for less toxic therapies has become greater.

The therapeutic strategies and methods described herein use anti-pre-B Cell Receptor (anti-pre-BCR) antagonists such as, for example, anti-pre-BCR antibodies. Intensified cytotoxic therapy for BCP-ALL almost universally leads to immune suppression and, consequently, complications that occur with opportunistic infections. These infections can claim the lives of 2% to 5% of newly-diagnosed patients, and 20% or more of patients who are treated in the relapse setting. Infection in particular is a cause of fatality in infants and Down Syndrome cases. Thus, this disclosure describes a therapeutic strategy that promotes and protects the existing mature B cell components of the adaptive immune system, rather than abrogating its protective effects.

Because healthy normal T cells and B cells often reside in G0/G1 phase resting status, and therefore are less exposed to chemotherapy-induced cell damage, it is possible to recruit healthy immune function in later stages of therapy. Such stages of therapy include the Consolidation Interim Maintenance and Maintenance phase, where bone marrow recovery and immune function return to near-normal states. This disclosure describes the use of pre-B Cell Receptor (pre-BCR) as a therapeutic target and the development of antagonist-based approaches as targeted therapies. These strategies target minimal residual disease (MRD), while protecting mature B cells and therefore favor a functional immune response to control opportunistic infections that otherwise pose significant mortality risks in BCP-ALL patients.

Figure 1:
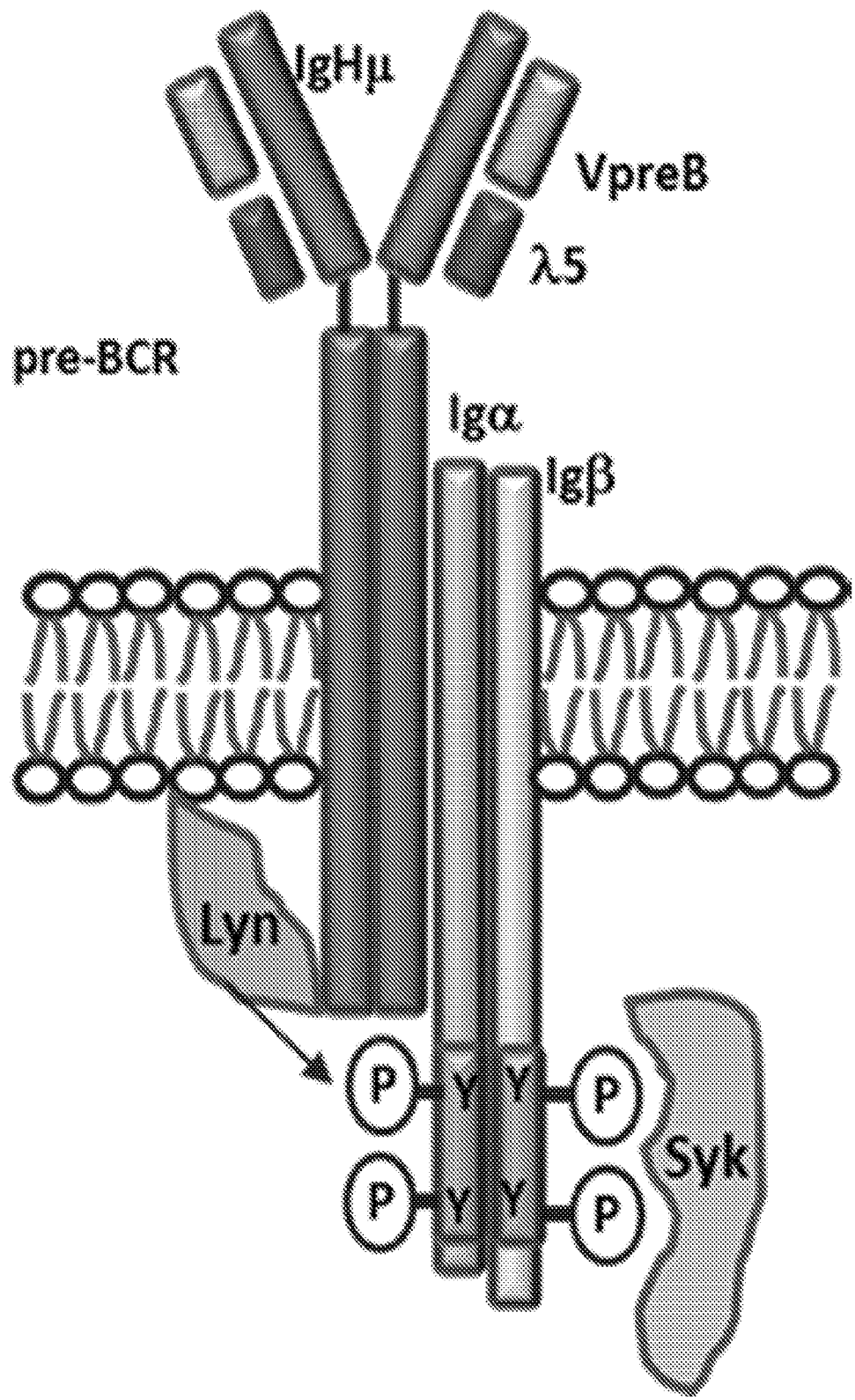
FIG. 1. The pre-BCR and its early signaling partners, Lyn and Syk.

FIG. 1 illustrates structural features of the pre-BCR, which generally includes a membrane Ig heavy chain (surface μ), surrogate light chain (CD179a, CD79b) and Igα and Igβ signaling subunits (CD79a, CD79b). Igα and Igβ each bear one ITAM (Immunoreceptor Tyrosine-based Activation Motif) in their cytoplasmic tails. After receptor aggregation, the ITAMs are phosphorylated by a src-family tyrosine kinase (Lyn) and then form binding sites for the dual $SH_2$-domains of spleen tyrosine kinase (Syk). Syk's recruitment is involved in propagating positive downstream signaling, regulating cell fate decisions. During normal B cell development, tonic signaling from the pre-BCR permits progression through the pro-B-cell-pre-B-cell checkpoints and completion of the IgL gene recombination process needed to assemble a fully functional B cell receptor. Tonic signaling from the pre-BCR is thought to be ligand-independent and mediated by self-oligomerization of the surrogate light chain components. In BCP-ALL cells, these homotypic encounters between pre-BCR may be transient but frequent—i.e., generating pro-survival signals that contribute to resistance to chemotherapeutic challenges.

Pre-BCR signaling can be enhanced through more stable crosslinking by soluble and stromal-bound galectin. Galectins are implicated in several hematologic malignancies, particularly MLL-rearranged BCP-ALL where expression of LGALS1 was linked to poor outcome. Members of the galectin family are bivalent or pentavalent; this feature mediates crosslinking when they bind receptor targets in soluble form. Because galectins can bind stromal elements, they likely also act in microenvironmental niches to support resistance to treatment and MRD. Galectin-mediated "clustering" of pre-BCR at stromal cell-blast synapses may be a very strong stimulus.

The therapeutic strategy described herein exploits the involvement of pre-BCR in early stages of B cell development. The identification of anti-pre-BCR antagonists (e.g., antibodies) can exploit techniques that allow one to screen large phage libraries for human antibodies that specifically bind the pre-BCR. (Sea Lane Biotechnologies, LLC, Mountain View, Calif.). Depending on their epitope specificity, these reagents may block homo-dimerization and/or galectin-binding. When this specificity is engineered into modified human IgGs, therapeutic antibodies can be developed that are capable of 1) recruiting immune effector cells, 2) blocking signaling and/or 3) delivering a payload. Alternatively, chimeric receptors can be composed of T cell receptor or other signaling receptors that contain ITAM (Immuno Tyrosine-Based Activation Motifs) for expression in T cells, as a means of T-cell mediated immunotherapy.

One advantage of using anti-pre-BCR antibodies over current immunotherapies (e.g., anti-CD19, anti-CD22, and/or anti-CD19-CAR) is that using anti-pre-BCR antibodies can spare mature B cells in the patient for functional adaptive immunity to opportunistic infections.

BCP-ALL cell lines and patient blasts were screened for sensitivity to kinase inhibitors selective for Syk, BTK, PI3K, and Jak2. Syk and PI3K inhibitors induced cell death in all patient samples tested, while Jak2 inhibitors arrested pre-B cells in the cell cycle. The effects of Syk and PI3K inhibitors are consistent with pre-BCR constitutively generating proliferative and pro-survival signaling in leukemia blasts. Because of the importance of these kinases in most leukocytes, targeting the pre-BCR directly can provide more highly specific therapy, which can further protect normal immune cell function in infants and children.

Figure 2:
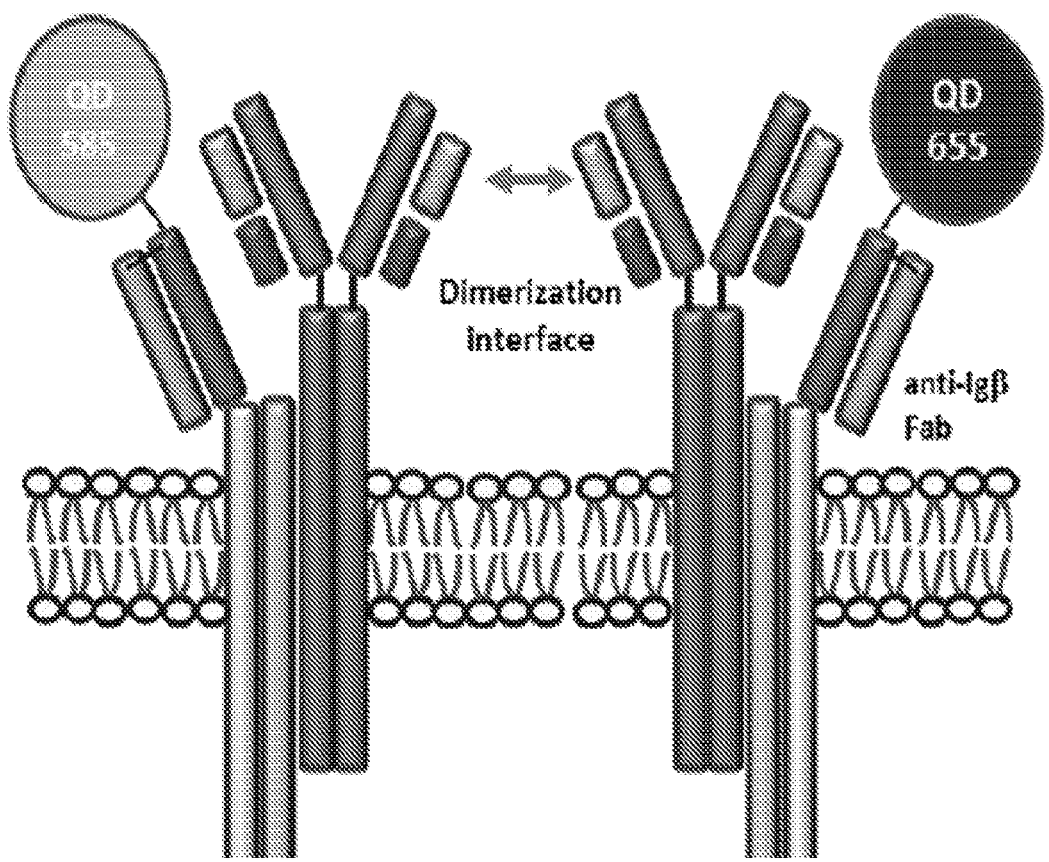
FIG. 2. A) Use of Fab-conjugated quantum dots (QD655, QD585) for 2-color tracking of pre-BCR oligomerization kinetics. B) Use of FPLC size exclusion chromatography (Superdex 75 10/300) to isolate α-Igβ Fabs (Fraction C) from bivalent fragments (Fraction B). C) Commassie-stained gel indicating yield of Fabs in Fraction C from FPLC. D) Purification of biotinylated Fab fragment as detected by western blot with streptavidin-HRP.
Figure 2:
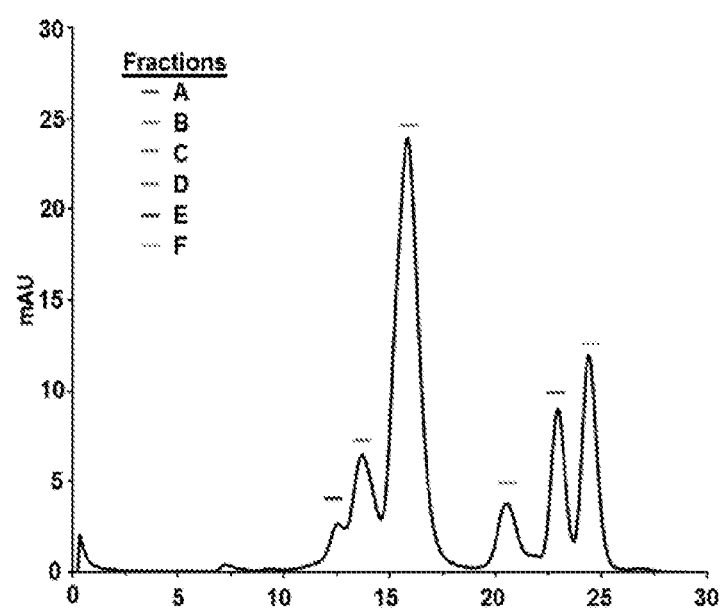
Figure 2:
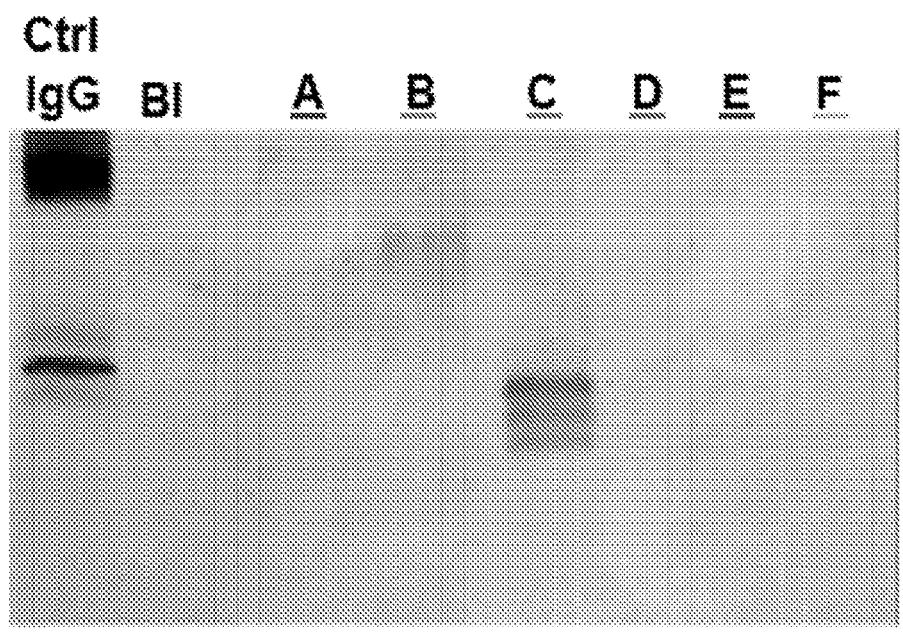
Figure 2:
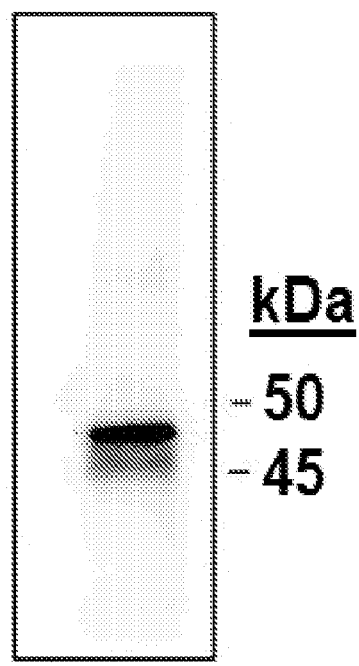

Single molecule tracking has emerged as a sensitive method to directly observe and measure protein-protein interactions in cell membranes. FIG. 2A illustrates how this technology allows one to measure the frequency and lifetime of pre-BCR homotypic aggregation kinetics. Stable Fab fragments of an anti-CD79b monoclonal antibody were generated (FIG. 2B and FIG. 2C) that can target the extracellular domain of Igβ (FIG. 2B). The Fab has been tagged with biotin for conjugation with avidin-Quantum Dots (QDs), a step that requires careful titration to ensure the 1:1 stoichiometry needed to ensure that the QD probe remains monovalent.

Figure 9:
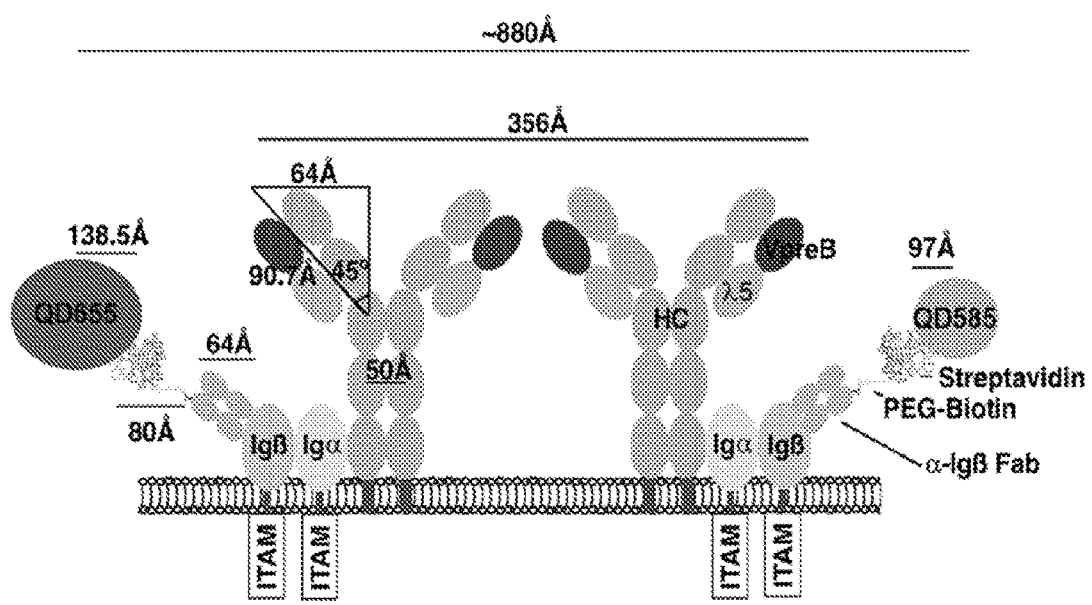
FIG. 9. Direct evidence of pre-BCR dimerization on surface of pre-B ALL cells. A) Experimental model with estimation of interaction distance based upon pre-BCR crystal structure (pdb code: 2H32), streptavidin (pdb code 1STP) and estimated QD radii. B) Time lapse image sequence (20 frames/s) indicates serial engagement over a period from 2 to 15 seconds. C) Viterbi plot of the most likely state (dimer, domain, free) between two QD interactions as derived from hidden Markov model with separation distance as the observed parameter. D) Two-channel 3D trajectory of anti-Igβ Fab-QD655 (top line) and Fab-QD585 (bottom line) show two receptors serial engaging repeatedly over 15 seconds with several instances of correlated motion before separating toward end of acquisition. E,F) A significant drop in displacement (top line, jump magnitude) and degree of uncorrelated motion (bottom line) as a function of separation distance seen with both 697 (left) and Nalm6 (right) cell lines at 100 nm and 200 nm, respectively. G,H) State specific diffusion between HMM determined states (free and dimer) shows a reduced diffusion in cell lines in the dimer state. (I,J) Dimer lifetime distribution with estimated off-rate as predicted by the HMM model with interaction distance and domain size of 100 nm and 300 nm, respectively.
Figure 9:
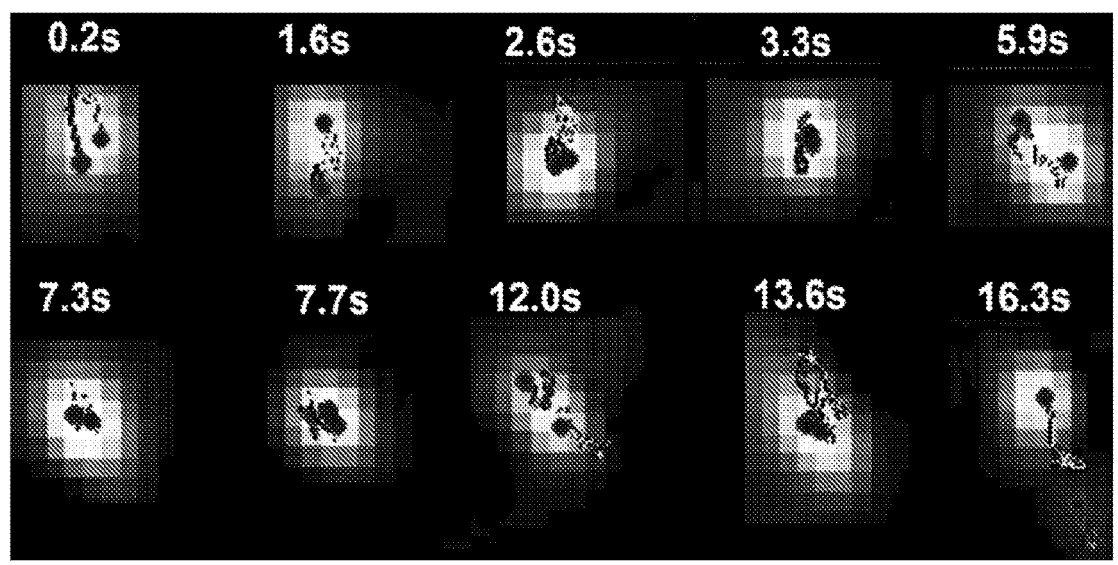
Figure 9:
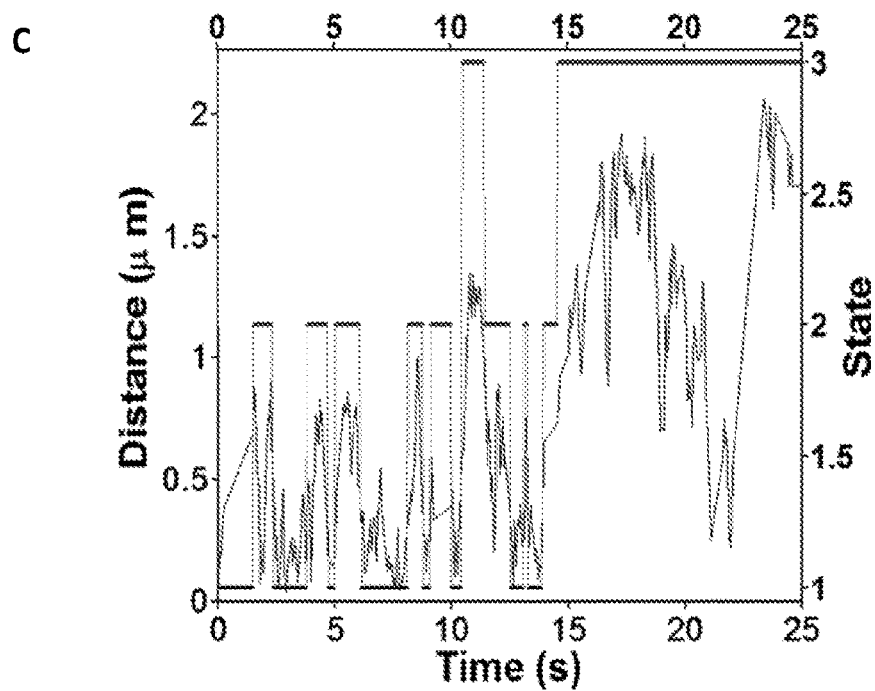
Figure 9:
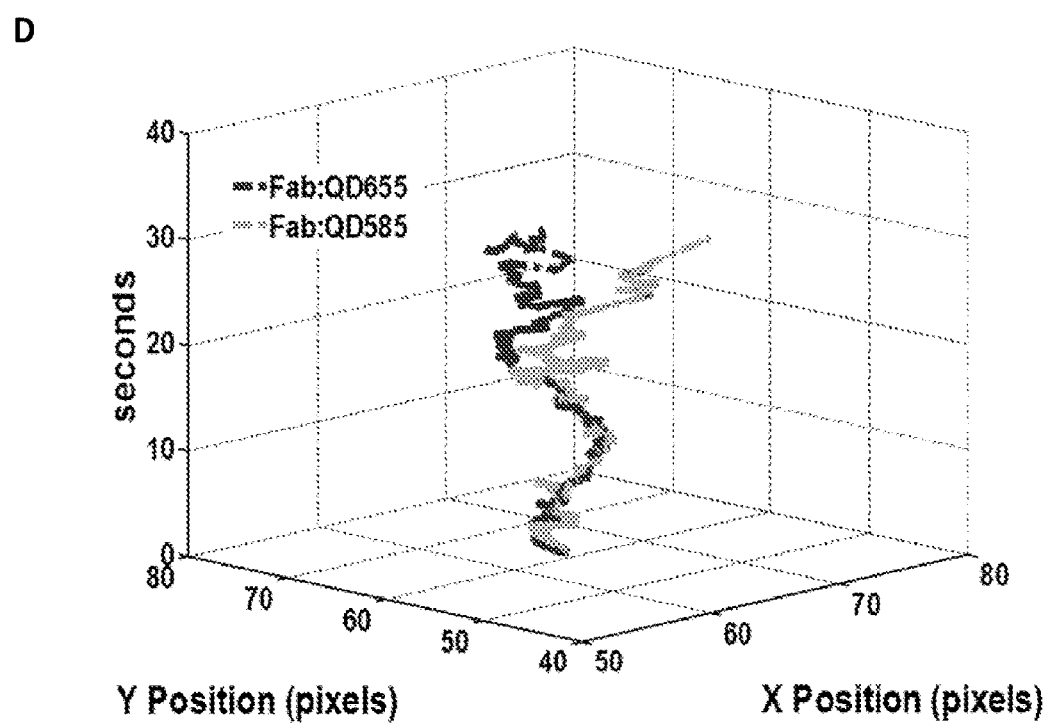
Figure 9:
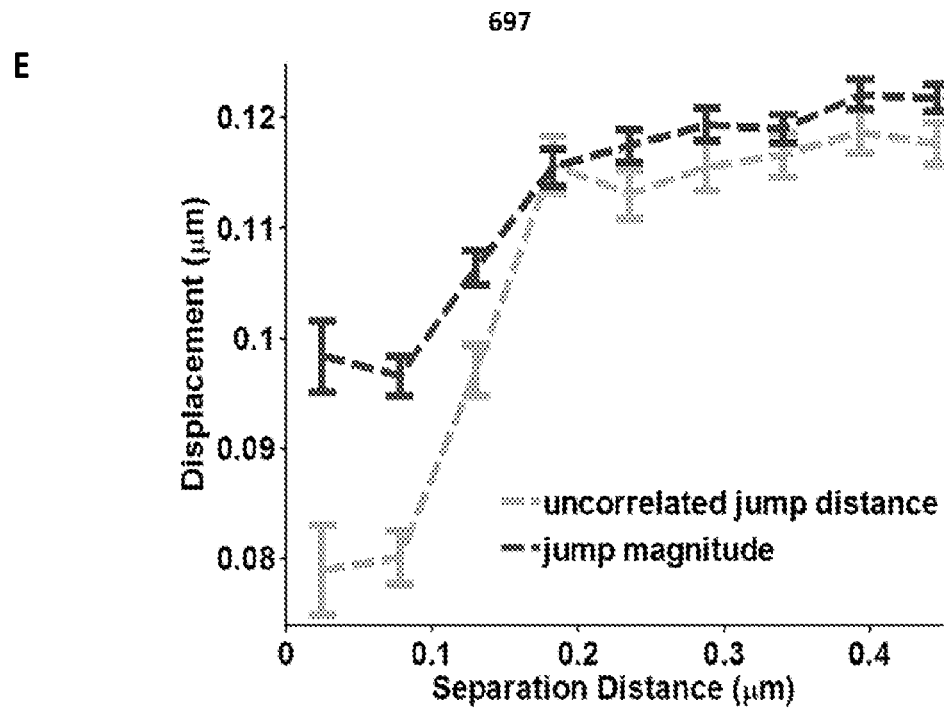
Figure 9:
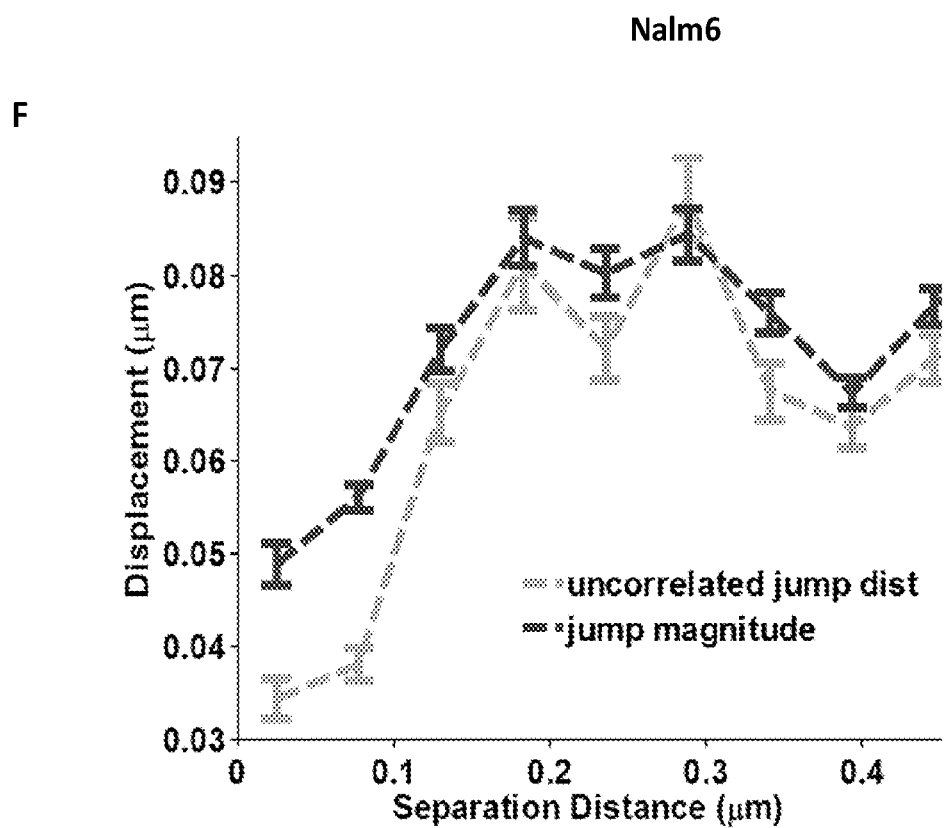
Figure 9:
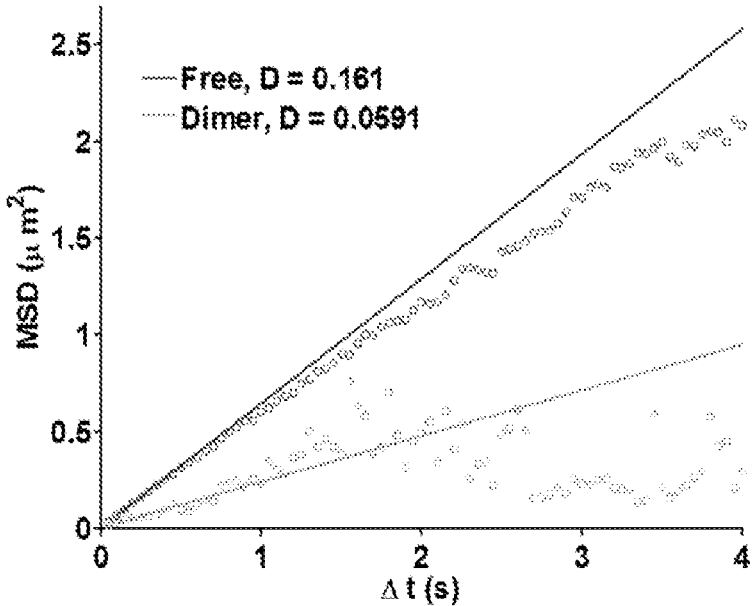
Figure 9:
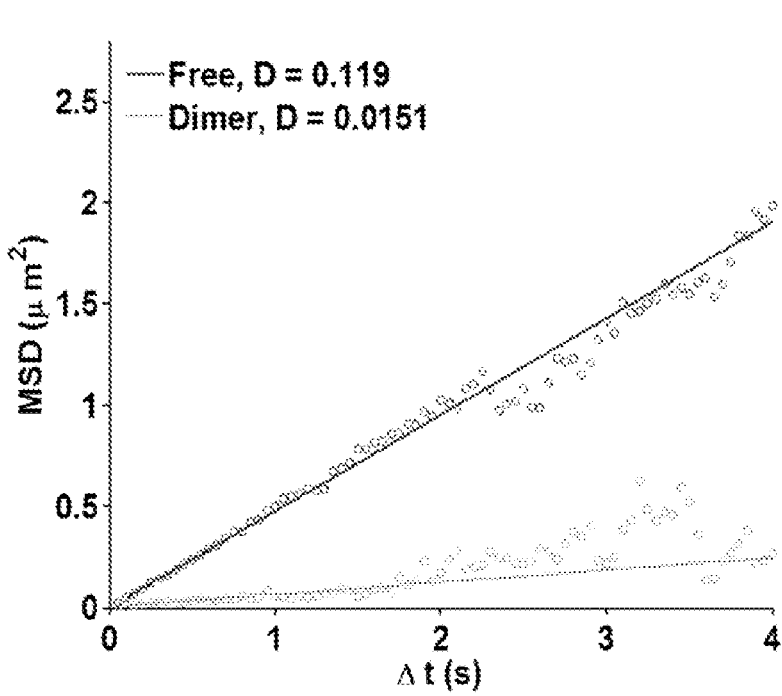
Figure 9:
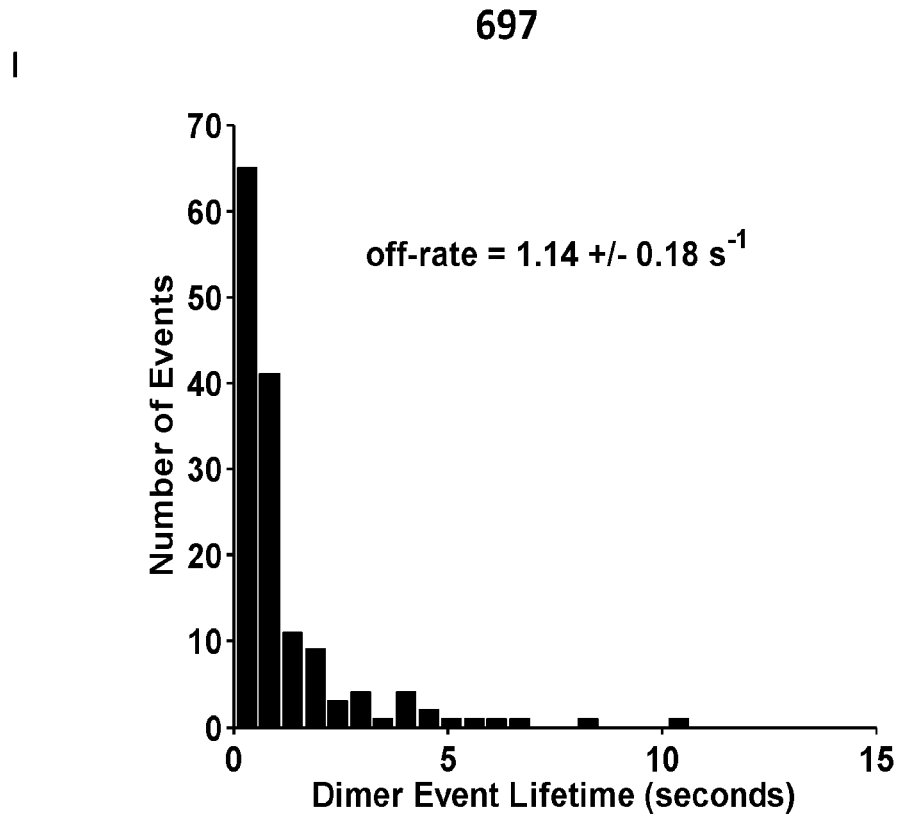
Figure 9:
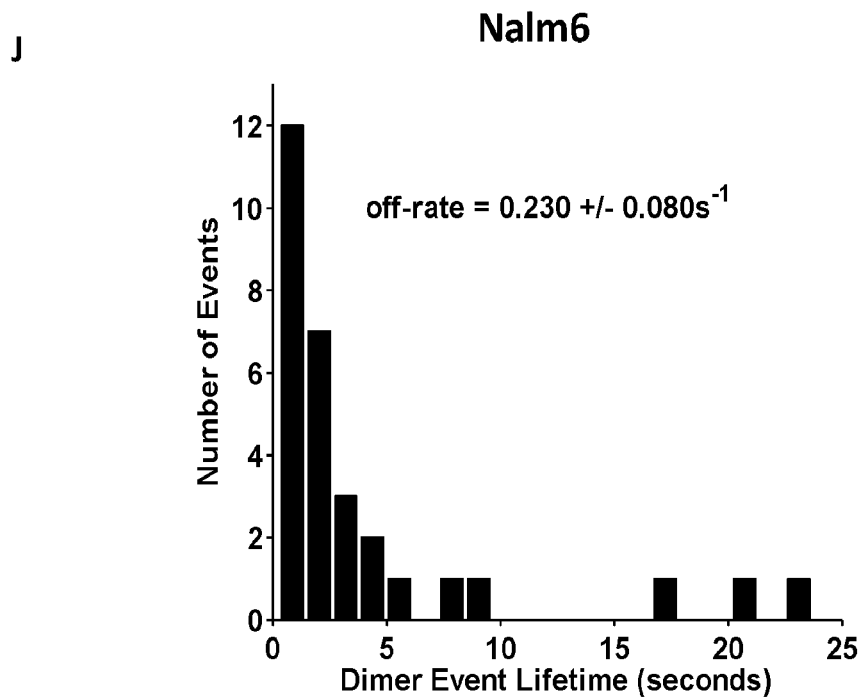

The brightly fluorescent QDs were then added to the medium of live cells in imaging chambers, where they bound to cell surface pre-BCR and allow tracking of interactions between sparsely-tagged receptors in real time. FIG. 9 shows that pre-BCR engage in homo-typic interactions on live BCP-ALL cells and that these interactions are highly dynamic.

FIG. 9A provides a detailed illustration of the strategy for observing pre-BCR dimerization through Single Particle Tracking (SPT). FIG. 9B illustrates an example of SPT imaging that captures pre-BCR dimerization in real time on the surface of live 697 cells (a cell line derived from a BCP-ALL patient (Findley et al., 1982, *Blood* 60:1305-1309). The pair dissociates and rebinds several times in the interval between 8-20 seconds, before they diffuse away as monomers in separate directions across the cell surface. The Viterbi plot in FIG. 9C reports the state-specific transitions of these two receptors over time, as defined by a hidden Markov Model (HMM) previously described in detail (Low-Nam et al, 2011, *Nat Struct Mot Biol* 18:1244-1249). For this pair, homo-interaction lifetimes are short (<3 sec).

The 3D diagram in FIG. 9D illustrates another view of the same pre-BCR dimer pair shown in FIG. 9C. The 3D plot illustrates the relative X and Y positions of each anti-Igβ Fab-QD probe over time. Based upon their close proximity and correlated motion, the two pre-BCR are dimerized at the beginning of imaging. Their dissociation at approximately 10 seconds is readily apparent, followed by short re-engagement, then dissociation and diffusion in separate directions toward the end of the image acquisition period.

Plots in FIG. 9E and FIG. 9F provide additional evidence that pre-BCR undergoes homotypic interactions on live cells. This is demonstrated by characteristic drops in uncorrelated motion (bottom lines) and jump magnitude (top lines) as a function of close separation distances. These analyses were performed for 697 cells (FIG. 9E), as well as for Nalm6 cells (FIG. 9F; Hurwitz et al., 1979, *Int J Cancer* 23:174-180). These data provide statistically rigorous validation that pre-BCR dimerization occurs frequently on the surface of two distinct BCP-ALL cell lines. The sharp decline in uncorrelated jump distance begins between 150 nm and 200 nm, potentially indicating that pre-BCR form chains and larger homo-oligomers. Cytogenetics and expression of BCP-ALL cell surface markers for both cell lines are found in Table 1.

TABLE 1

Characteristics of pre-ALL cell lines

| | 697 | Nalm6 | Patient 280 | Patient 238 |
|---|---|---|---|---|
| CNS Status | n/a | n/a | CNS2B | CNS2C |
| Ploidy Index | 1 (diploid) | 1 (diploid) | 0.92 (hypodiploid) | 1 (diploid) |
| BCL6 | + | + | + | + |
| CD3 | − | − | − | − |
| CD10 | + | + | + | − |
| CD13 | − | + | − | − |
| CD19 | + | + | + | + |
| CD20 | + | nd | Subset | − |
| CD22 | + | + | + | dim subset |
| CD34 | − | + | large subset | + |
| CD37 | − | − | nd | nd |
| CD38 | + | nd | nd | nd |
| CD45 | − | nd | − | − |
| CD79a | + | + | + | + |
| CD80 | − | − | nd | nd |
| CD138 | − | + | nd | nd |
| TdT | + | + | + | + |
| HLADR | + | + | + | + |
| Cytogenetics | TCF3-PBX1, 46, XY t(1; 19)(q23; p13) del(6)(q21) | ETV6-PDGFRB, 46, XY t(5; 12) (q33.2; p13.2) | 46, XY[4] | MLL-AF4, 46, XY, t(4; 11)(q21; q23) [cp6]/49, XY, +X, +1, t(4; 11)(q21; q23), +2 1[5]/46, X, -Y, t(4; 11)(q21; q23), +mar[3] |

Data in FIG. 9G and FIG. 9H compare the relative mobility of pre-BCR monomers and dimers on the surface of both cell lines. In the free state (top line), pre-BCRs have a relatively fast diffusion coefficient (0.16 µm$^2$/sec on 697 cells and 0.12 µm$^2$/sec on Nalm6 cells). By comparison, diffusion rates for interacting pairs of pre-BCR (representing jump distributions only during the intervals when they are self-associated) are markedly slower at 0.059 µm$^2$/sec on 697 cells and 0.015 on Nalm6 cells. The average mean square displacement (MSD) values (i.e., not state-specific) calculated for pre-BCR on these cells are similar using either the anti-Igβ or the anti-mIgµ QD probes. The average MSD values for pre-BCR diffusion in 697 and Nalm6 cells are 0.129 µm$^2$/sec and 0.09 µm$^2$/sec, respectively. These data are significant for at least two reasons. First, the data provide definitive evidence that pre-BCR homotypic interactions occur. Second, the data show that these interactions are dynamic based upon stochastic processes for their dissociation, resulting in a characteristic range of dimer lifetimes representing all binding and unbinding events within a data set (FIG. 9I and FIG. 9J).

Figure 10:
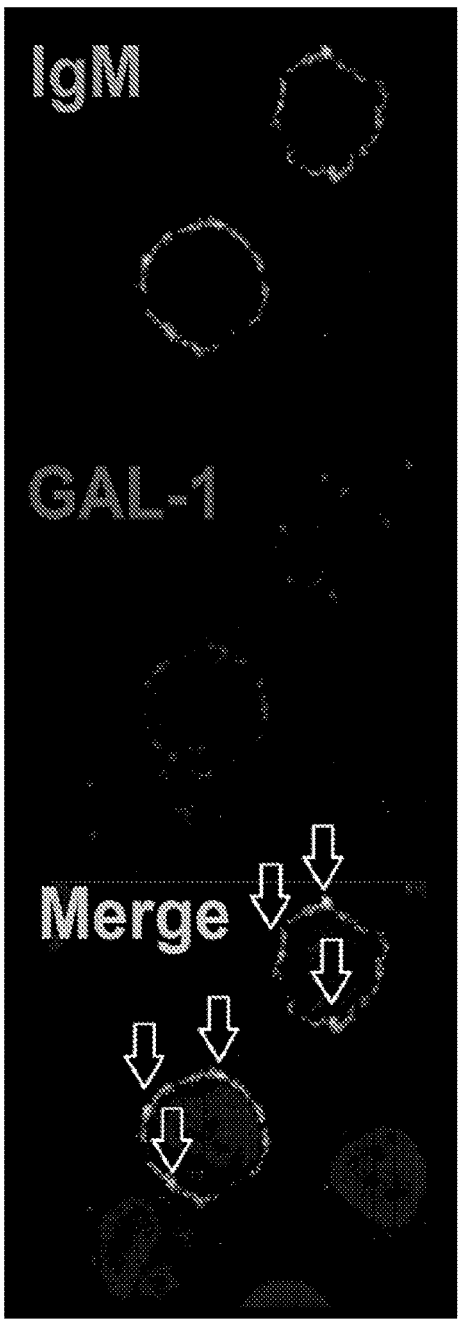
FIG. 10. Galectin-1 stabilizes dimerization and promotes formation of higher order complexes. A) Binding of labeled galectin-1 (red) and pre-BCR (green). Arrows indicate cluster formation and co-localization with pre-BCR. B,C) Blocking carbohydrate binding domain of galectin-1 with 10 mM lactose treatment shows clear differences in displacements for uncorrelated jump distance and jump magnitude of distinct anti-Igβ probes at different separation distances. D) Incubation with 10 mM lactose in galectin-1 treatment results in overall increase in diffusion of the pre-BCR. E) Treatment of 697 cells with sodium orthovanadate plus $H_2O_2$ blocks constitutive activity of phosphatases to build up levels of phospho-Syk (Y352) under tonic signaling conditions (10-minute, 20-minute, or 30-minute treatment with pervanadate alone). Accumulation of phospho-Syk Y352 in the presence of pervandadate is enhanced by treatment with galectin +/− lactose but not by galectin alone.
Figure 10:
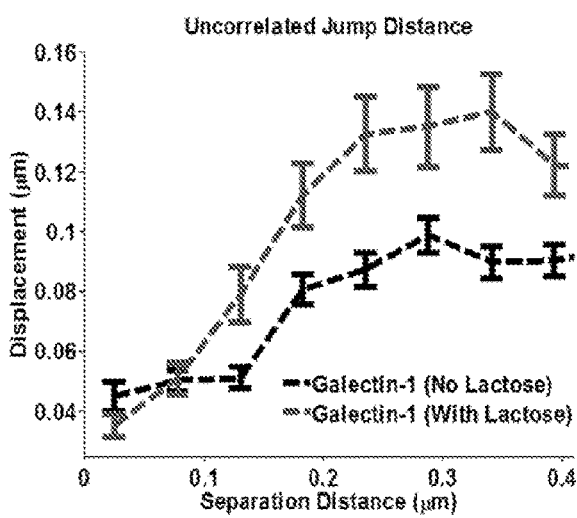
Figure 10:
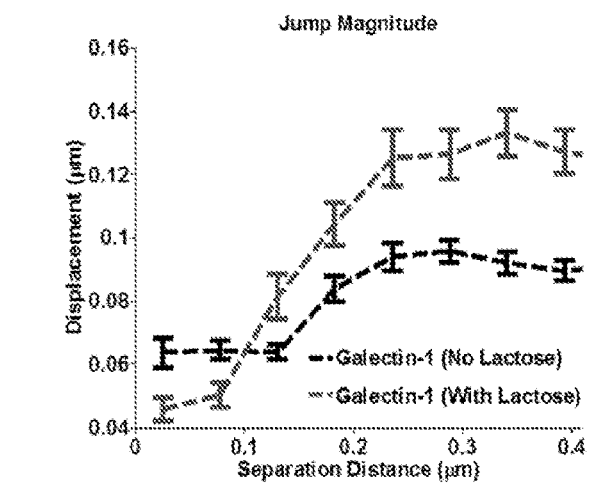
Figure 10:
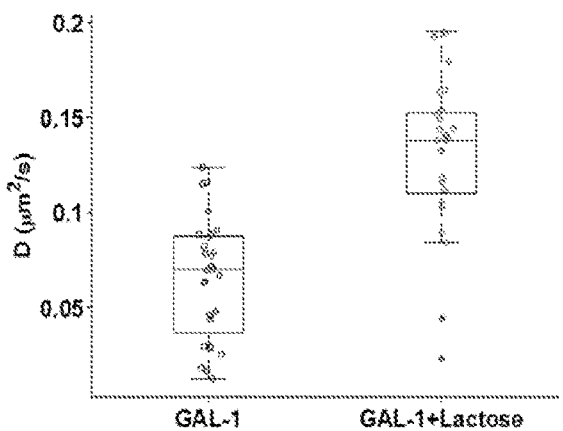

Although pre-BCR lack classical "ligands", they can be activated by proteins that aggregate them through binding to the surrogate light chain components. This is illustrated in FIG. 10A, which shows that incubation of 697 cells with Alexa 555-conjugated galectin-1 (red) leads to marked clustering of the pre-BCR (green) within five minutes. The merged image shows significant co-localization (yellow) for galectin-1 and the pre-BCR in these clusters. For these experiments, galectin-1 was used at a concentration of 10 µM since at this concentration soluble galectin-1 should be at least 90% in the dimer state. Single Point Tracking was performed using anti-Igβ Fab-QD probes in order to evaluate the effects of galectin-1 on pre-BCR diffusion. FIG. 10B and FIG. 10C show a marked drop in both jump magnitude and uncorrelated motion for pre-BCR on the surface of galectin-1-treated 697 cells. A large fraction of pre-BCR become essentially immobile (FIG. 10D).

The marked slowdown of the pre-BCR bound to galectin-1 can be attributed, at least in part, to carbohydrate-mediated lattices with other glycoproteins. This is shown in the data in FIG. 10, from experiments performed in the presence of excess lactose (10 mM) to block the lectin binding site of galectin-1. Under these conditions, larger overall jump distributions for diffusing receptors (top line, FIG. 10B) and a shorter interaction distance for the onset of correlated motion were observed (bottom line, FIG. 10C). Overall diffusion of galectin1-crosslinked pre-BCR was markedly faster in the presence of lactose (FIG. 10D), approaching values for pre-BCR under tonic signaling conditions.

Moreover, antagonists targeting the pre-BCR (e.g., anti-VpreB antibodies) may provide additional advantages if, for example, the antibodies also effectively block galectin binding and consequent activation of the pre-BCR. This disclosure specifically includes pre-BCR antagonists that block galectin-mediated activation of the pre-BCR, in the case where galectin is a soluble, dimerized ligand or in the case where galectin is presented to BCP-ALL cells in the context of stromal cells.

Molecular stimulations of the pre-BCR structure can form the basis of designing pre-BCR antagonists that block homo-interactions and/or galectin-mediated crosslinking. Starting with the amino acid sequence from a wide range of biologic modulators targeting pre-BCR or galectin-1, 3D molecular models can be constructed by homology modeling (MODELLER, University of California San Francisco, San Francisco, Calif.; ROSETTA, Rosetta Commons.org) using coordinates from high resolution structural information with high sequence and/or 3D identity. Top candidates can then be selected scoring algorithms such as Discrete Optimized Protein Energy (DOPE) score, FIG. 3A. Best homology models of biologic antagonists can then be used as the basis for docking (GRAMM-X, Tovchigrechko et al., 2006, *Nucleic Acids Res* 34(Web Server issue):W310-314; ZDOCK, Pierce et al., 2014, *Bioinformatics* 30(12):1771-

Figure 3:
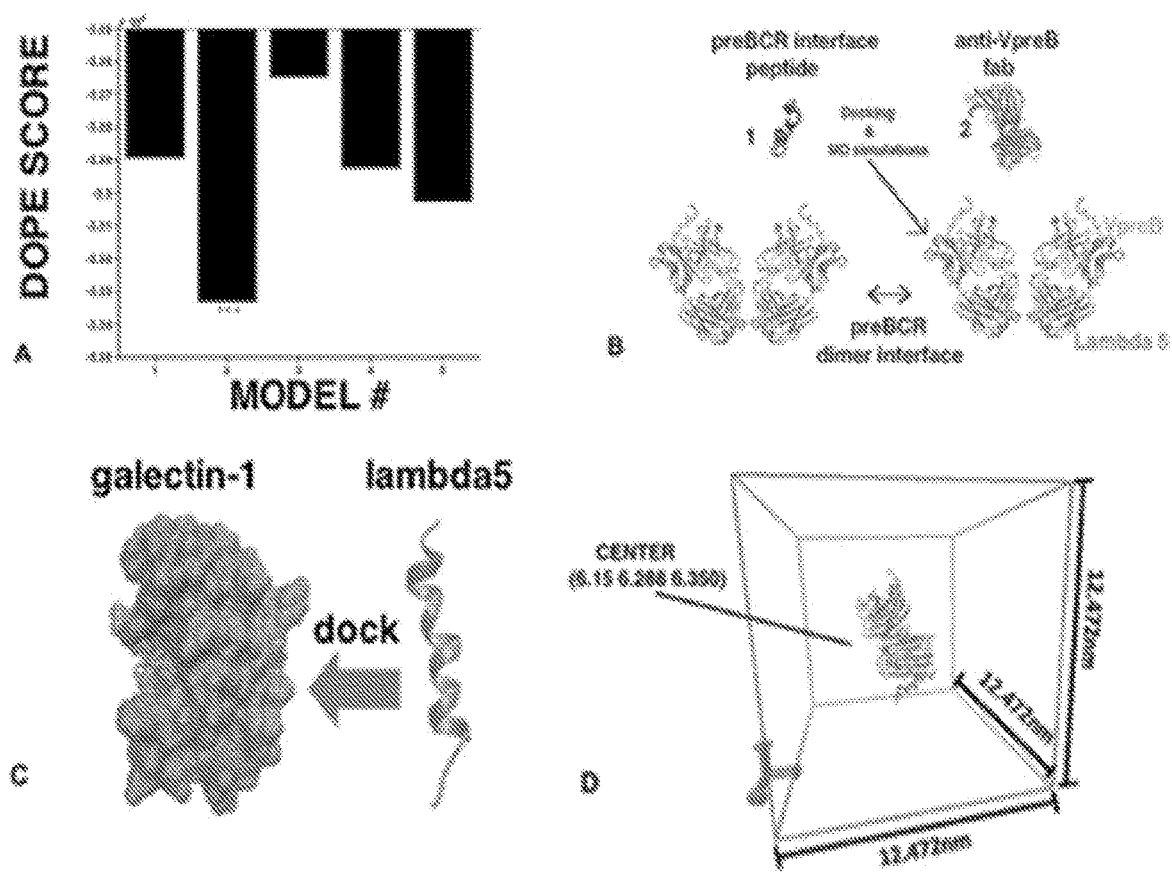
FIG. 3. A) Several different biologic antibody-based or peptide homology models are built using MODELLER algorithm. Top candidates are selected based upon Discrete Optimized Protein Energy (DOPE) score. B) Homology model proteins are docked (i.e. ZDock algorithm) to putative pre-BCR based upon model constructed form pre-BCR X-Ray structure (pdb code: 2H32). C) Similarly, homology modeling and molecular docking provide insight on antagonists that disrupt pre-BCR/galectin-1 interactions (pdb code: 2LKQ). D) Constructed models are placed in a simulation box that is filled with explicit solvent and subjected to energy minimization, NVT/NPT ensemble and production MD (i.e., steered molecular dynamics, umbrella sampling) using GROMOS or AMBER force fields to compare free energy binding among different designed pre-BCR modulators.

1773) into the established high resolution NMR or X-Ray structures of galectin-1 (pdb: 1W6O) or the pre-BCR (pdb: 2H32), respectively, FIG. 3B-C. These constructed models can then be incorporated into a simulation box (FIG. 3D) with periodic boundary conditions and surrounded by explicit solvent in preparation for molecular dynamic (MD) simulations. For MD simulations, one can use, for example, the GROMACS software (University of Groningen, Groningen, Netherlands) with GROMOS and/or AMBER force field. Molecular models are energy minimized with steepest descent algorithm and equilibrated with the appropriate NPT/NVT ensemble to maintain appropriate physiological pressures, density and temperature. Next, several different production molecular dynamics simulations techniques—e.g., steered molecular dynamics (SMD) or umbrella sampling (US)—can be performed over nanosecond to microsecond time scales to establish relative pull forces and free energy of binding. Other information—e.g., COM minimum distance, root mean square fluctuations (RMSF), root mean square deviations (RMSD), accessible surface area (SASA), and/or hydrogen bonding count—can also be measured to gain insight into the key molecular interactions taking place. One can select the most energetically favorable conformers for testing inhibitory molecules (e.g., therapeutic antibodies).

Figure 4:
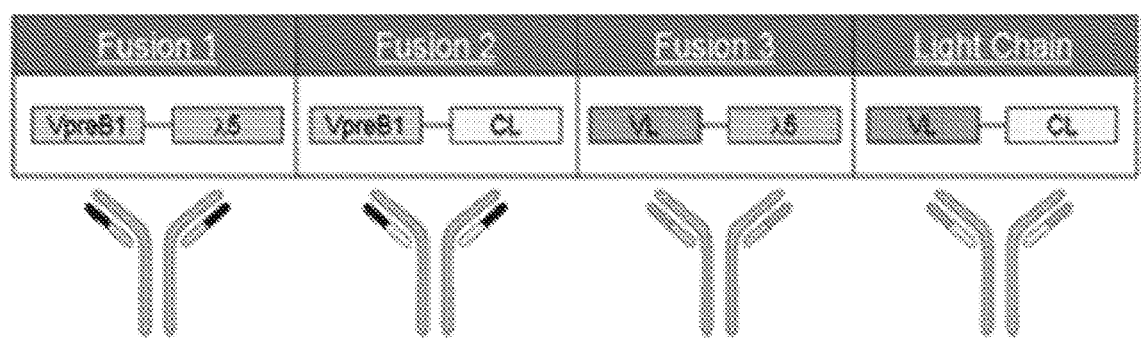
FIG. 4. Testing for VpreB binding specificity using IgG heavy chain paired with engineered surrogate or lambda 5 light chain variants.

A series of vectors that encoded soluble pre-BCR-like protein variants were engineered as described in more detail below. (Sea Lane Biotechnologies, LLC, Mountain View, Calif.). (FIG. 4). These formats included the native trimeric pre-BCR functional unit, including a functional human IgG1 heavy chain paired with the surrogate light chain components or a full length human IgG1 heavy chain paired with a single polypeptide chain that is a product of genetic fusion between the VpreB1 gene and the λ5 (Fusion 1). Variant polypeptides were constructed by eliminating either one or both peptide extensions of the λ5 N-terminal and the VpreB1 C-terminal. All of the resulting "Surrobodies" were expressed by co-transfection of a functional human Heavy chain isolated from an anti-influenza H5N1 hemagglutinin antibody with the components of the pre-BCR trimer or its fusion variants in mammalian cells. In addition, a polypeptide containing the VpreB1 fused to a constant lambda (Fusion 2) was made as well as a polypeptide containing a variable Lambda chain fused to the λ5 (Fusion 3) were made.

The Contextual Combinatorial Immune Repertoire (ConCIRT) Synthetic library was panned against recombinant Surrobody that included the functional anti-influenza H5N1 hemagglutinin heavy chain paired with the Fusion 1 version of the surrogate light chain. Phage panning begins with the propagation of ConCIRT library. The full library consists of 56 billion fully human, synthetically constructed antibodies arrayed in over 100 separate phage displayed sub-libraries. The heavy chain diversity derived from four human germ line VH genes (representing the two largest human VH families, VH1 and VH3) paired with four V kappa frame works genes and five V lambda framework genes. Phage bound to target protein coated on 96-well microtiter plate were eluted and titered. The resulting eluates were amplified for use in the subsequent round of panning. After four rounds of phage panning, individual clones from enriched phage pools were analyzed for specific binding by ELISA assay.

Clones were tested for their ability to bind bacterial expressed anti-PLGF Surrobody with the Fusion 1 construct as the heavy chain partner. To assess specific binding of selected clones to the VpreB1 (SEQ ID NO:2) or the λ5 chains, the anti-flu heavy chain was paired with either Fusion 2 or Fusion 3. Testing for VpreB1 binding specificity was performed on ELISA plates coated with E. coli-derived heavy chain paired with the Fusion 2 construct. For λ5 specificity binding, E. coli-expressed heavy chain paired with the Fusion 3 construct.

Specific hits in crude bacterial lysates were determined by detection with an HRP-conjugated anti-myc antibody. Following the positive ELISA hit identification, specific clones were sequenced. 16 anti-VpreB1 unique antibodies were recovered that specifically recognize the VpreB1 chain protein (SEQ ID NO:2). This set of specific monoclonal antibodies show great sequence diversity using different germ lines for both heavy and light chains using both kappa and lambda subtypes. All phage derived antibodies were found to specifically recognize the VpreB1 polypeptide (SEQ ID NO:2). This set of specific monoclonal antibodies show great sequence diversity that includes four different VH frame works of the heavy chains paired with light chains of both kappa and lambda subtypes. All 16 phage-derived antibodies were found to specifically recognize the VpreB1 polypeptide (CD179a; SEQ ID NO:2) of the surrogate light chain (Table 2).

TABLE 2

| Summary of selected Fab hits isolated from ConCIRT antibody phage library | | |
|---|---|---|
| Human heavy chain | Human light chain (Kappa) | Human light chain (Lambda) |
| VH1 | 4 | 3 |
| VH3 | 5 | 4 |

The specific recognition of these antibodies against pre-BCR epitopes within the VpreB1 is a significant finding. The VpreB1 shares a low sequence homology with other human Ig variable domains and therefore offers an advantage over antibodies that recognize an epitope within the λ5 component that shares much higher sequence homology with the human Ig lambda constant region. Binding to the VpreB1 chain ensures an efficient and specific binding to the pre BCR expressed on malignant cells, with no binding to circulating IgG molecules and therefore reduces the likelihood sink and elimination of therapeutic mAb that may be bound to circulating human Ig/λ molecules. Binding affinities of a lead antibody are shown in Table 3.

TABLE 3

| Binding Affinity of anti-Human VpreB1 IgG to SgG | | | | |
|---|---|---|---|---|
| Run | SA Biosensor Immobilization | Binding Titration Format | $K_D$ [nM] | kobsRsq |
| 1 | 0.75 µg/ml S2g αHGF_biotin | 100 µg/ml αVpreB_IgG | 0.280-0.100 | 0.979-0.998 |
| 2 | 0.75 µg/ml S2g αHGF_biotin | 50 µg/ml αVpreB_IgG | 0.120-0.066 | 0.981-0.998 |

TABLE 3-continued

Binding Affinity of anti-Human VpreB1 IgG to SgG

| Run | SA Biosensor Immobilization | Binding Titration Format | $K_D$ [nM] | kobsRsq |
|---|---|---|---|---|
| 3 | 0.75 µg/ml αVpreB_IgG_biotin | 50 µg/ml S2g αHGF | 0.048-0.016 | 0.967-0.988 |

Figure 5:
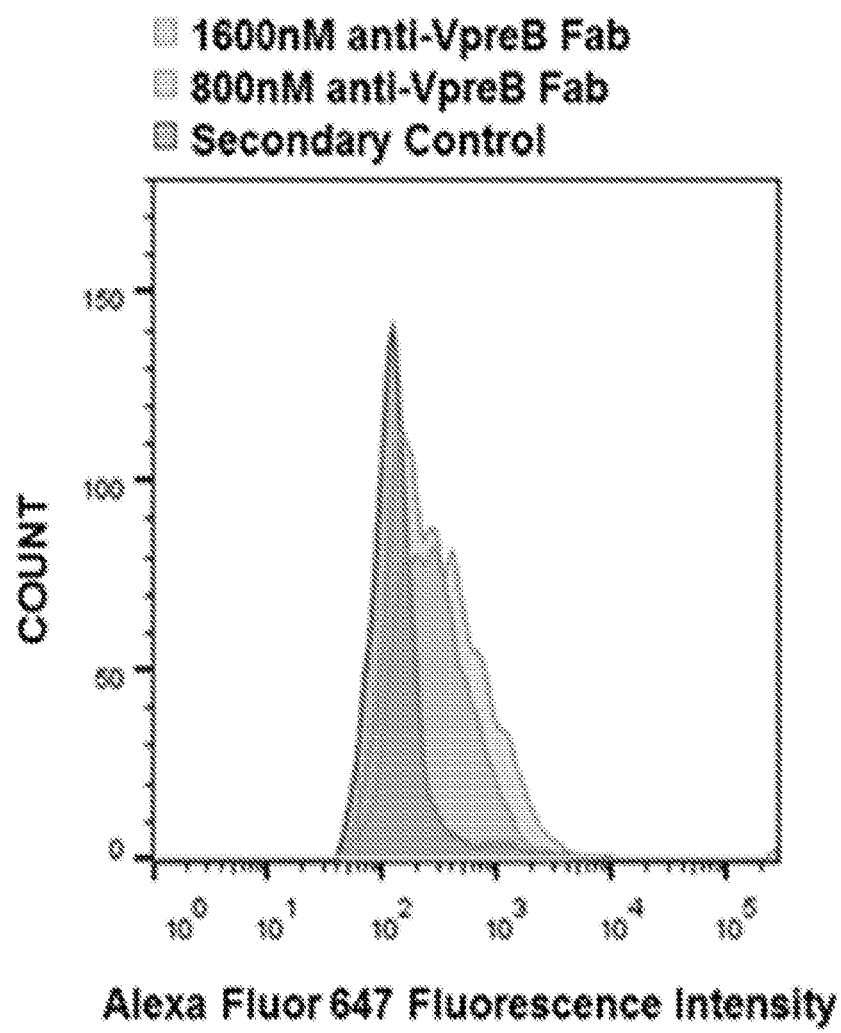
FIG. 5. A) Data showing anti-VpreB1 Fab bind to live pre-B ALL cells (697 cell line). B) Internalization of intact anti-VpreB IgG is slow and dose dependent. C) Data showing subnanomolar binding of intact, Alexa 647-conjugated VpreB IgG to live cells.
Figure 5:
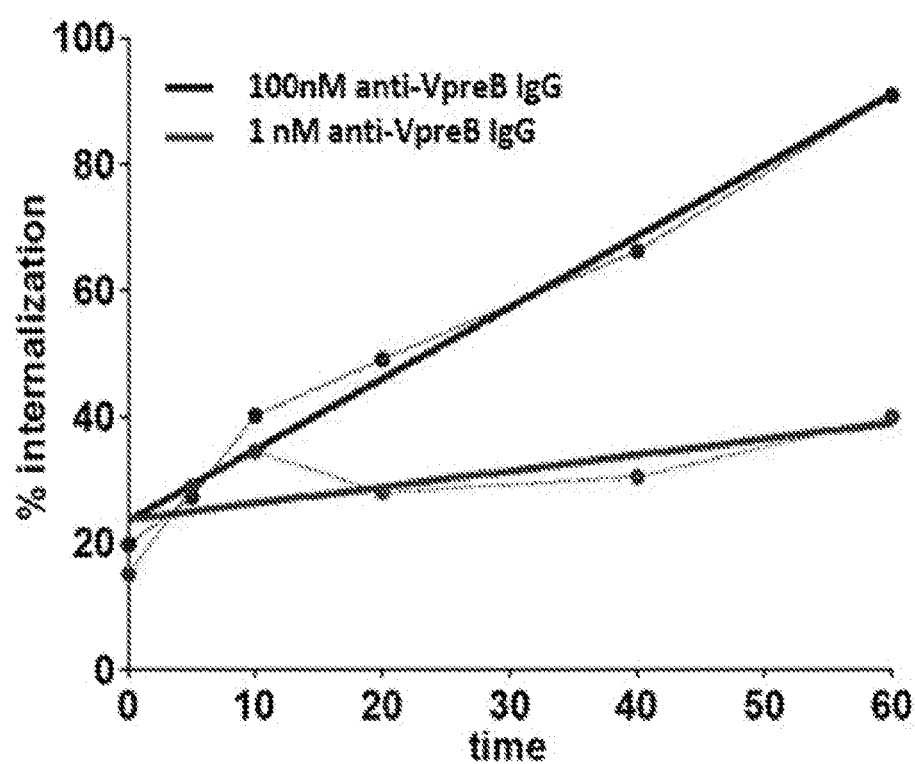
Figure 5:
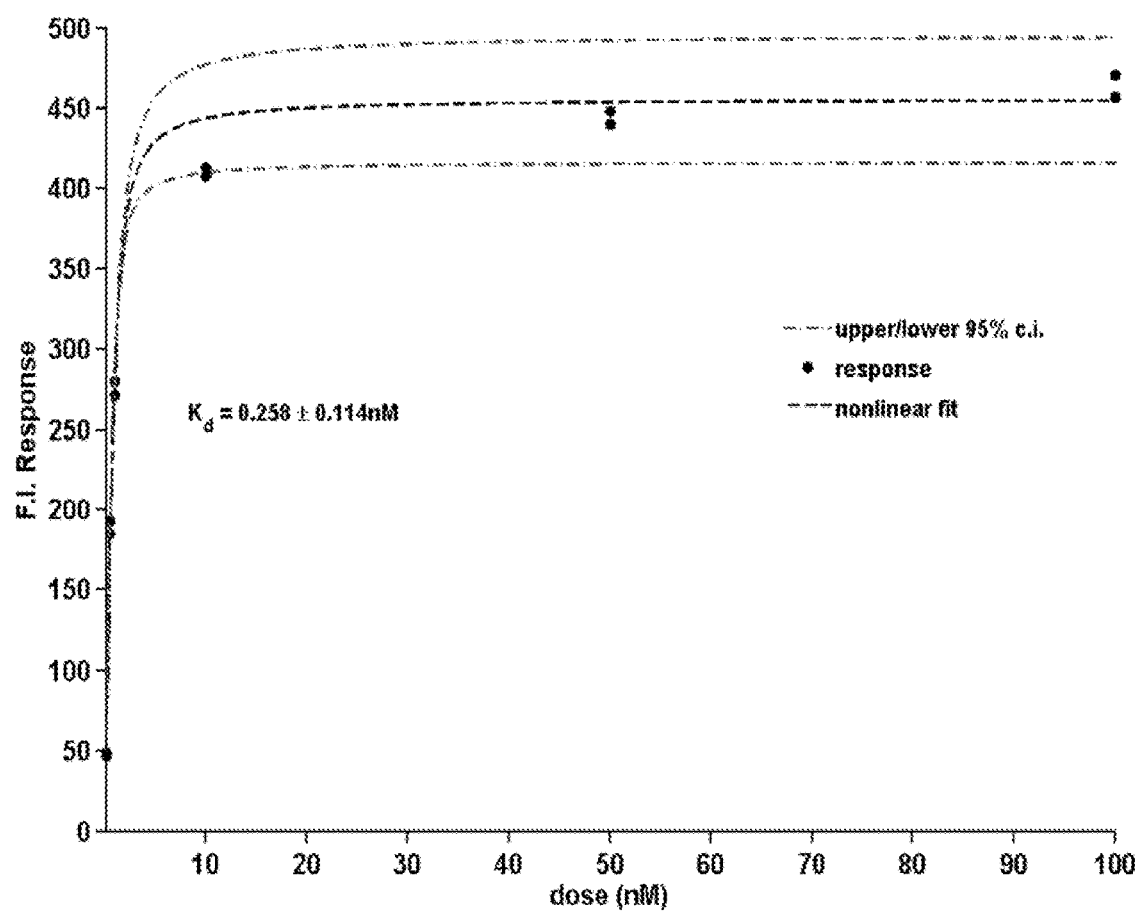
Figure 6:
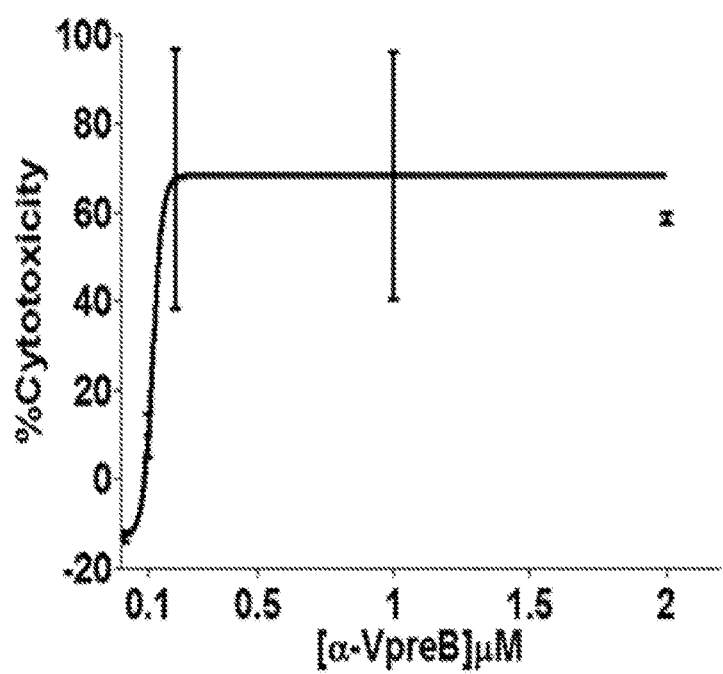
FIG. 6. Data showing anti-VpreB1 IgG opsonization of leukemia cells supports human NK cell killing in vitro (ADCC) and is dose dependent. A) NK-mediated killing of BCP-ALL cells (Cytotox 96® nonradioactive cytotoxicity assay from Promega). B) NK-mediated killing of BCP-ALL cells (7AAD flow assay for cell viability)
Figure 6:
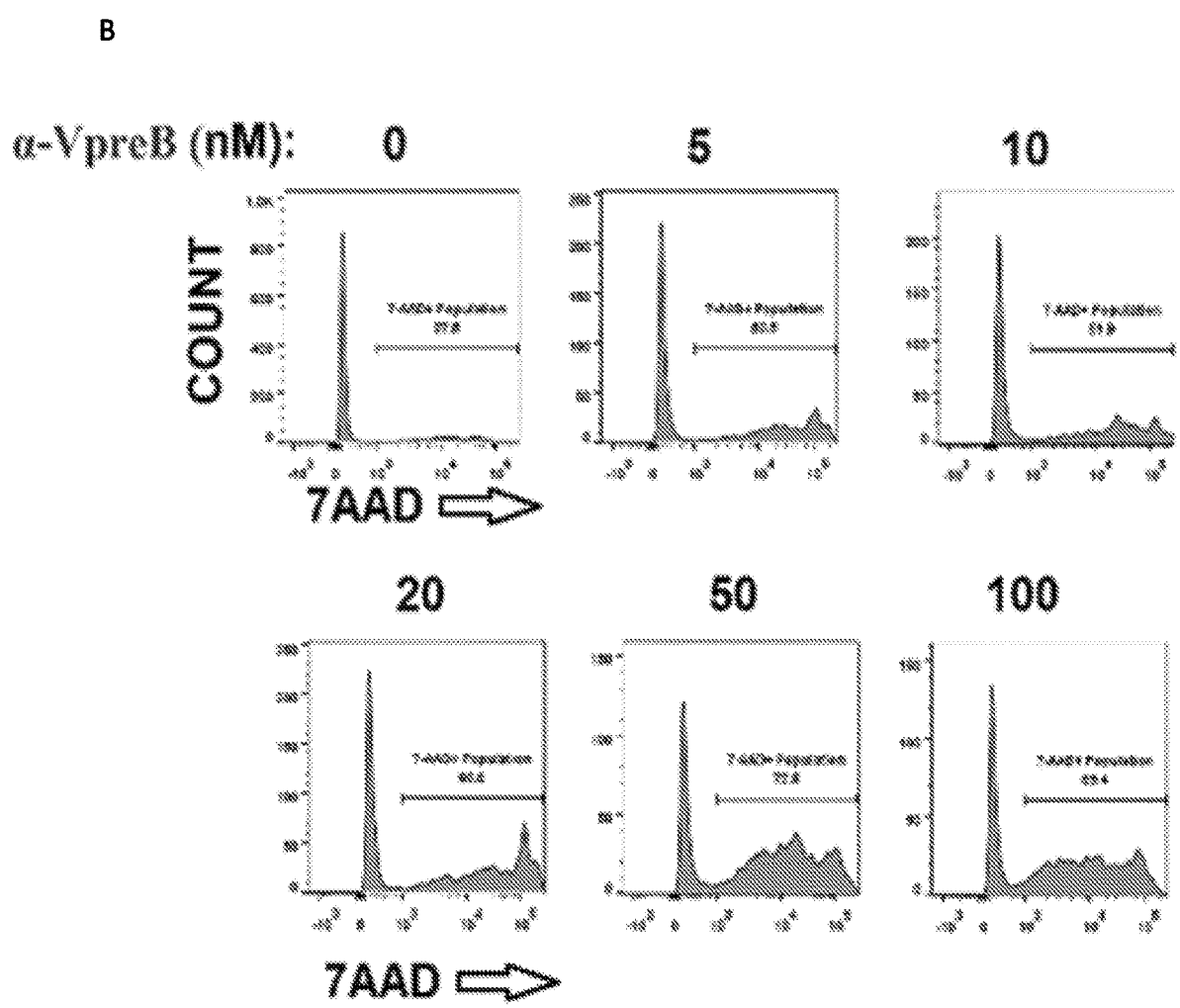

Confirmation that anti-pre-BCR antibodies bind to the pre-BCR on live leukemia cells is provided in FIG. 5. Results in FIG. 5A provide flow cytometry measures of anti-VpreB1 (Fab fragments) binding to live pre-B (697) cells. Fab fragments were incubated for 15 minutes at 37° C. at concentrations of either 800 nM or 1600 nM, followed by 15 minute room temperature treatment with secondary anti-κ light chain conjugated to Alexa Fluor 647 (Life Technologies, Grand Island, N.Y.). There is a marked shift in fluorescence intensity relative to cells treated with secondary antibody controls. Results in FIG. 5B and FIG. 5C show that intact anti-VpreB1 IgG also bind with subnanomolar affinity and internalize into BCP-ALL cells in a dose-dependent manner.

All 16 Fabs were produced and tested for their relative binding affinity in ELISA assay format. The hallmark of the relative affinity ELISA is the use of gradient of coated antigen concentration raw wise across the plate. The affinity range for this group of Fabs was evaluated between 0.85 nM for the highest affinity binder down to 250 nM of the lowest affinity binder.

Figure 11:
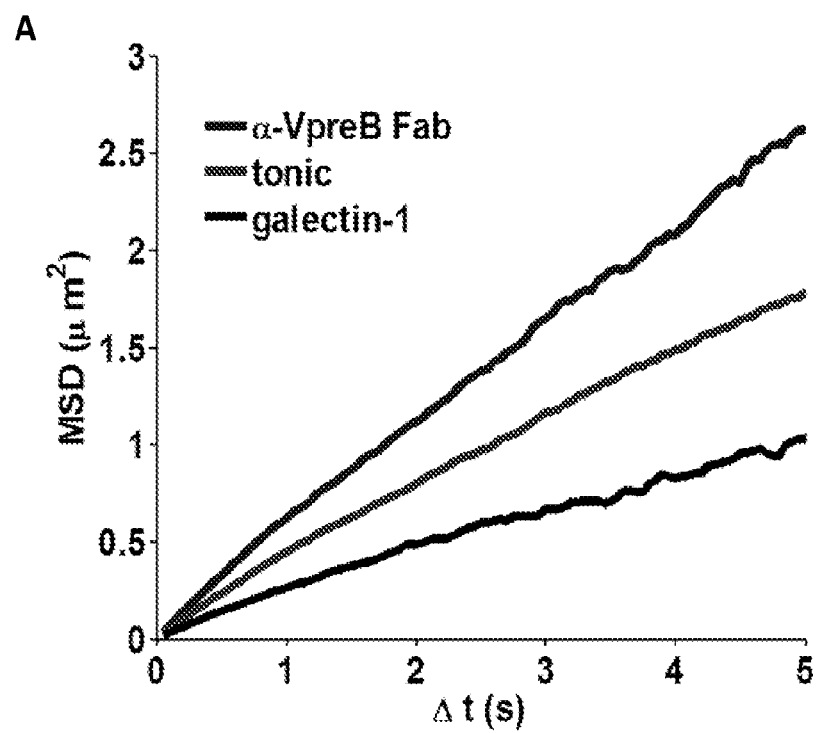
FIG. 11. Comparison of VpreB Fabs and Galectin treatments on ensemble measurements for pre-BCR diffusion and dimerization. A) Overall Mean Square Displacement (MSD) values show a marked increase in pre-BCR diffusion with the anti-VpreB Fab (1 μM, top line) relative to tonic signaling (middle line), indicative of dimer disruption. In contrast, pre-BCR crosslinking for 10 minutes with galectin-1 (10 μM, bottom line) markedly slows receptor diffusion. B) Clear differences can be seen in the distribution of the diffusion coefficient as gathered from individual sequence files under various treatment conditions. C) 10-minute treatment with anti-VpreB Fab (1 μM) disrupts pre-BCR homotypic interactions, as demonstrated by absence of a drop in uncorrelated jump distance (left, top line) and jump magnitude (right, top line) at short separation distances between two probes compared to tonic signaling (middle line). In contrast, 10-minute treatment with 10 μM galectin-1 promotes pre-BCR aggregation, as shown by a sharp drop in uncorrelated jump distance (left, bottom line) and jump magnitude (right, bottom line) at greater separation distances relative to tonic signaling.
Figure 11:
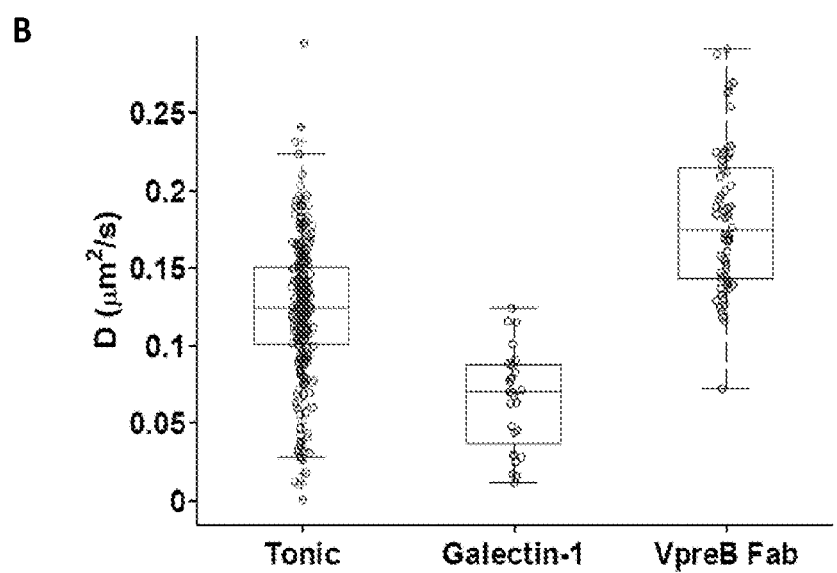
Figure 11:
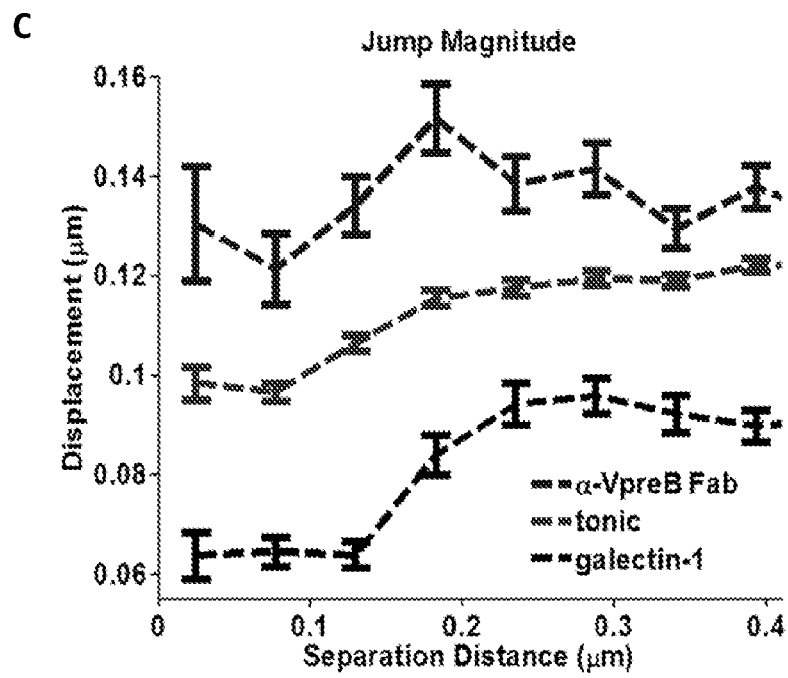
Figure 11:
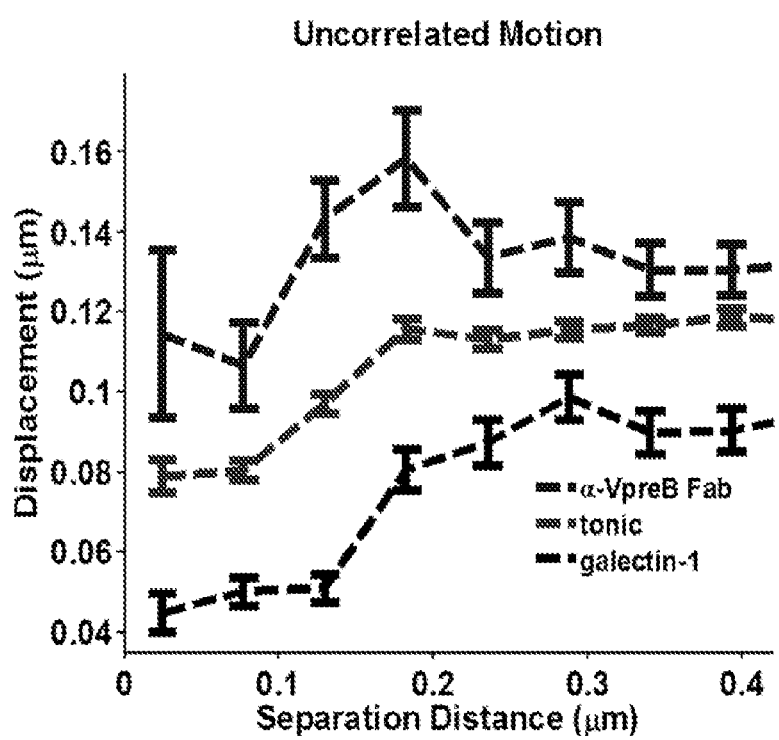

Data in FIG. 11A show that anti-VpreB1 Fabs block pre-BCR homotypic interactions. Data are reported as changed in ensemble diffusion coefficients (MSD) for pre-BCR plus and minus saturating levels of anti-VpreB1 Fabs (1 µM). In these experiments, Fabs were added to 697 cells for 15 minutes at 37° C. prior to performing Single Particle Tracking (SPT). Targeting the pre-BCR with the anti-VpreB1 Fab monovalent blocking reagents markedly increased the overall diffusion of pre-BCR. Box plots in FIG. 10B report summary findings, with VpreB Fab treatment leading to an absence of an immobile fraction (D<0.05 µm²/sec). For comparison, pre-BCR are far less mobile after treatment with galectin-1.

The plots in FIG. 11C provide an overall comparison of the changes in uncorrelated motion and jump magnitude for pairs of pre-BCR tracked on the surface of untreated cells (middle, under tonic signaling conditions) versus cells treated with the anti-VpreB Fabs (top lines) or galectin-1 (bottom lines). These data again show that pre-BCR self-association can be prevented by monovalent blocking antibodies against the surrogate light chain, while galectin-1 induces large-scale pre-BCR aggregation.

Figure 8:
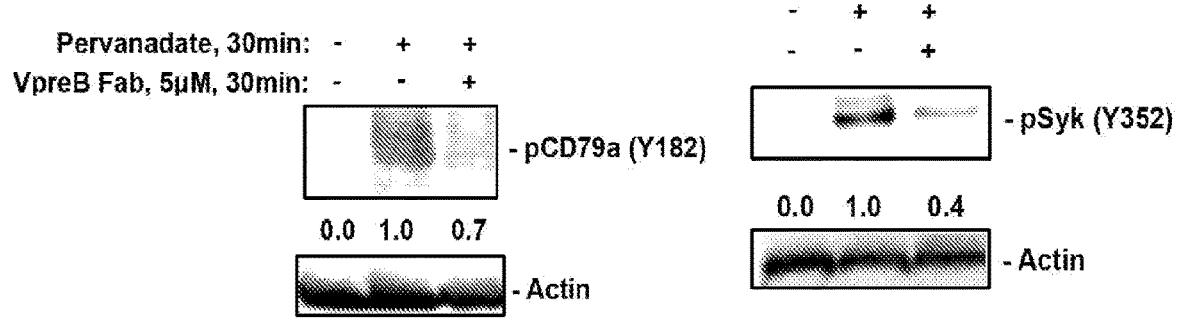
FIG. 8. Western blotting analysis of pre-BCR signaling, based upon phosphorylation of the CD79a ITAM or Syk as well as expression of BCL6. A) 30-minute blockade of the pre-BCR homo-dimerization interface with bulky anti-VpreB Fab (5 µM) reduces the accumulation of phospho-CD79a (Y182) and phospho-Syk (Y352) in the presence of pervanadate. B) 24-hour treatment with anti-VpreFab ablates the expression of BCL6. C) Incubation of 697 cells with Bay-61-3606 and/or dasatinib results in decreased accumulation of phosphorylated CD79a (pY182) and Syk (pY352) in the presence of pervanadate. D) Dasatinib treatment for 24 hours inhibits BCL6 expression. SHIP-1 inhibition with 3-a-aminocholestane (3AC) also results in a decrease in BCL6 levels after 24 hours, while the Jak inhibitor tofacitinib results in an increase in BCL6 protein levels. E) 30-minute treatment with 3AC enhances accumulation of phospho-Syk in the presence of pervanadate; tofacitinib had no effect on Syk phosphorylation under the same conditions.
Figure 8:
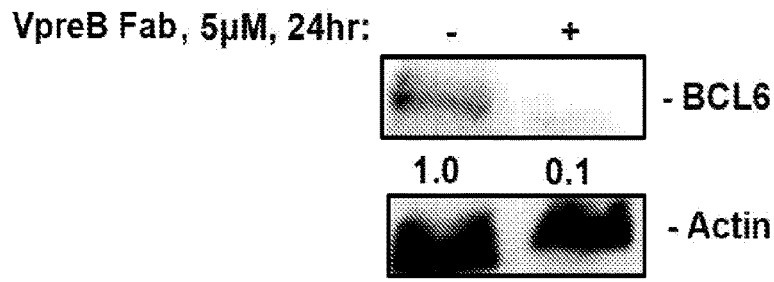
Figure 8:
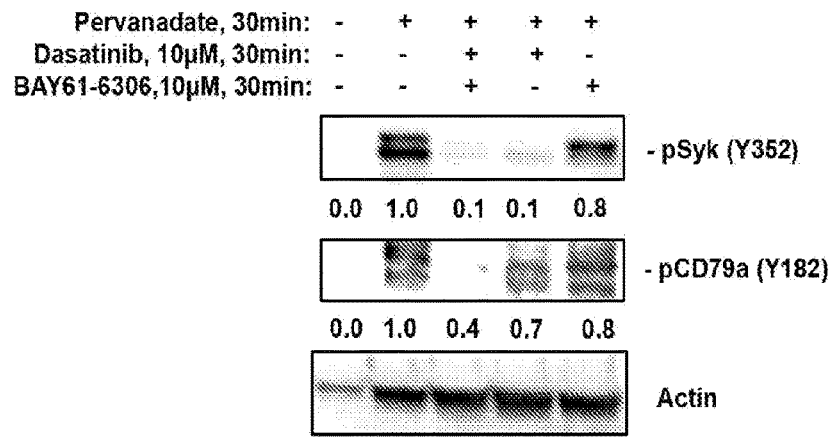
Figure 8:
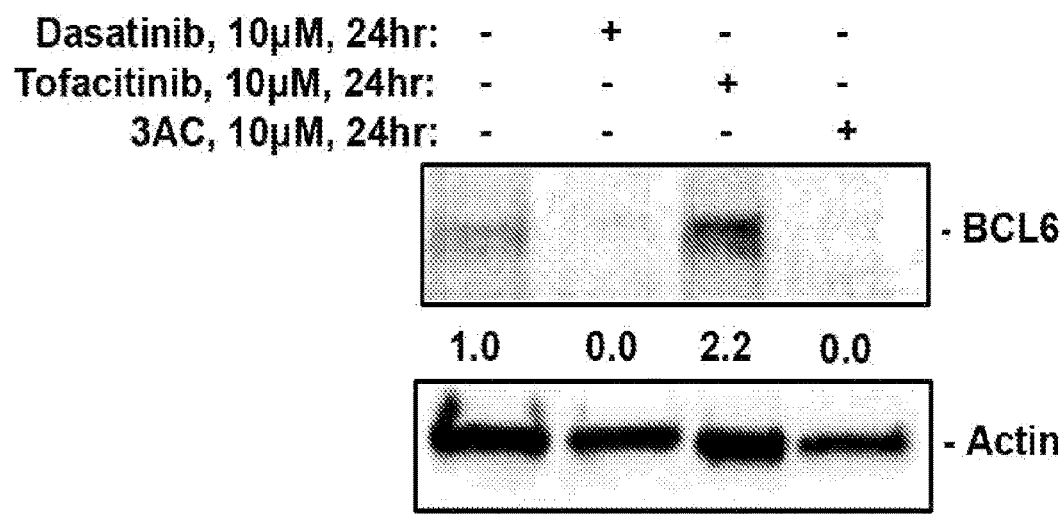
Figure 8:
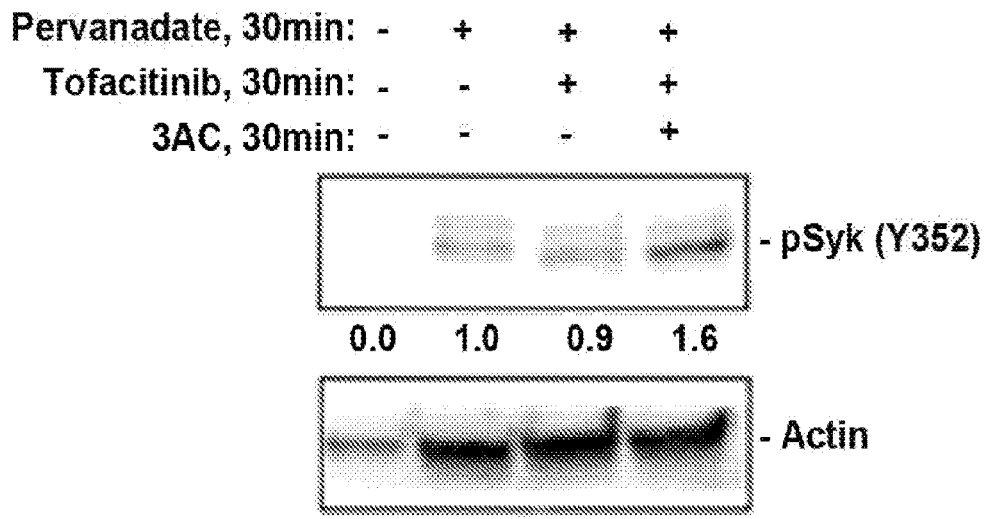

Results in FIG. 8 evaluate the ability of anti-VpreB Fabs, as well as inhibitors directed at pre-BCR downstream signaling partners Lyn, Syk and SHIP1 (INPP5D), to block tonic signaling from the pre-BCR. As shown in FIG. 8A, 30-minute treatment of cells with anti-VpreB Fabs blocked the accumulation of phospho-Igα (CD79a) ITAM and phospho-Syk in the presence of pervanadate. As shown in FIG. 8B, BCL6 expression was also blocked after overnight treatment with anti-VpreB Fabs that inhibit homo-interactions.

FIG. 8C shows that adding dasatinib to pervanadate-treated 697 cells blocked Lyn-mediated phosphorylation of CD79a involved in recruiting and activating Syk. The combination of the Syk inhibitor, Bay-61-3606, and dasatinib completely blocked the accumulation of phospho-CD79a during phosphatase inhibition, suggesting that trans-phosphorylation by Syk combines with Lyn activity for full phosphorylation. The Syk inhibitor also diminished accumulation of Syk PY352 by approximately 20%, consistent with this tyrosine as a substrate of both Lyn and Syk. The pre-BCR-Lyn-Syk axis involvement in tonic signaling to BCL6 expression is clearly demonstrated since overnight treatment with dasatinib abolished BCL6 levels. Treatment of 697 cells with the Jak inhibitor, tofacitinib, did not alter Syk phosphorylation in the presence of pervanadate (FIG. 8E). Overnight treatment with tofacitinib led to elevated levels of BCL6 in 697 cells, consistent with release of Jak-mediated repression of BCL6 (FIG. 8D). Treatment of cells with the SHIP1 inhibitor slightly elevated Syk phosphorylation (FIG. 8E) and completely repressed the expression of BCL6 (FIG. 8D). These results further support the conclusion that pre-BCR tonic signals, including the downstream signaling partner SHIP, support BCP-ALL survival.

Results in FIG. 6, FIG. 8 and FIGS. 11-13 illustrate that intact and Fab anti-VpreB antibodies have effects on live BCP-ALL cells. If required, affinity maturation of the antibodies can also be accomplished through mutagenesis and rescreening. The best candidates can be tested for the ability to block pre-BCR dimerization and/or galectin binding (in the single molecule tracking assay), signaling (by western blotting), and/or induce apoptosis (by flow).

Figure 12:
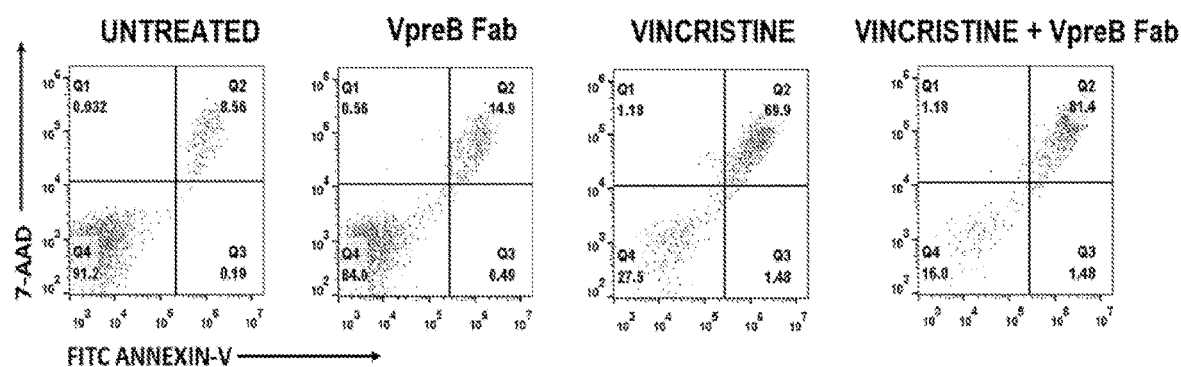
FIG. 12. A) Prolonged incubation of 697 cells with α-VpreB Fabs (5 μM) modestly enhances apoptosis alone or when combined with low dose vincristine (10 ng/ml). B,C) Enhanced apoptosis seen in 697 cells when administered with cell-permeable kinase inhibitors (dasatinib, Bay-61-3606, tofacitinib, 3AC) in combination with vincristine.
Figure 12:
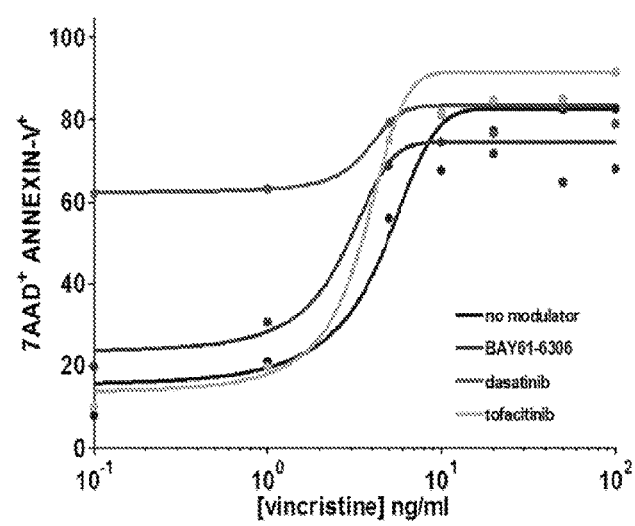
Figure 12:
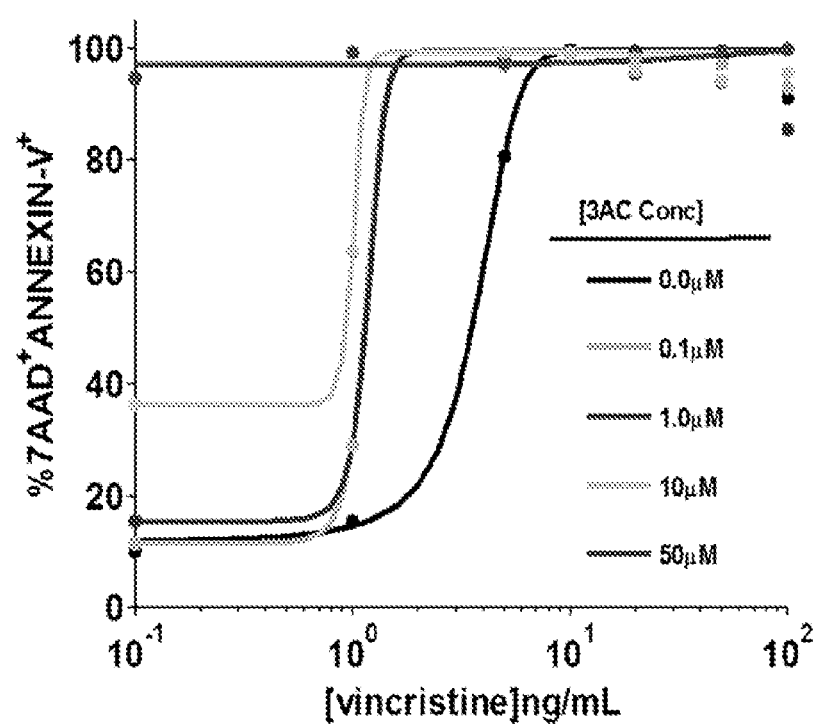

Since blocking pre-BCR pro-survival signaling may be advantageous for chemo-sensitization, one can compare apoptosis alone or in combination with a sub-lethal dose of a chemotherapeutic such as, for example, vincristine or daunorubicin. For example, overnight incubation of cells with VpreB Fabs slightly enhanced 7-AAD and Annexin-V labeling of the cells (14.9% of cells, compared to basal levels of 8.5%, FIG. 12A). The combination of VpreB Fabs with 10 ng/ml vincristine also slightly enhanced apoptosis (81.4% apoptotic cells, compared to 69.9% for vincristine alone). Consistent with these results, cell-permeable kinase inhibitors (e.g., dasatinib, Bay-61-3606, tofacitinib, and 3AC) also potentiate apoptosis in cells treated with vincristine over a range of doses (FIG. 12).

As shown for the initial anti-VpreB studies, all of the scFv can be reengineered for expression as intact, bivalent antibodies (scFv₂-human Fc) and evaluated for binding and clustering of the pre-BCR, induction of pre-BCR endocytosis, and/or ability to recruit human NK cells and macrophages in vitro for antibody-mediated cytotoxicity or phagocytosis.

Figure 13:
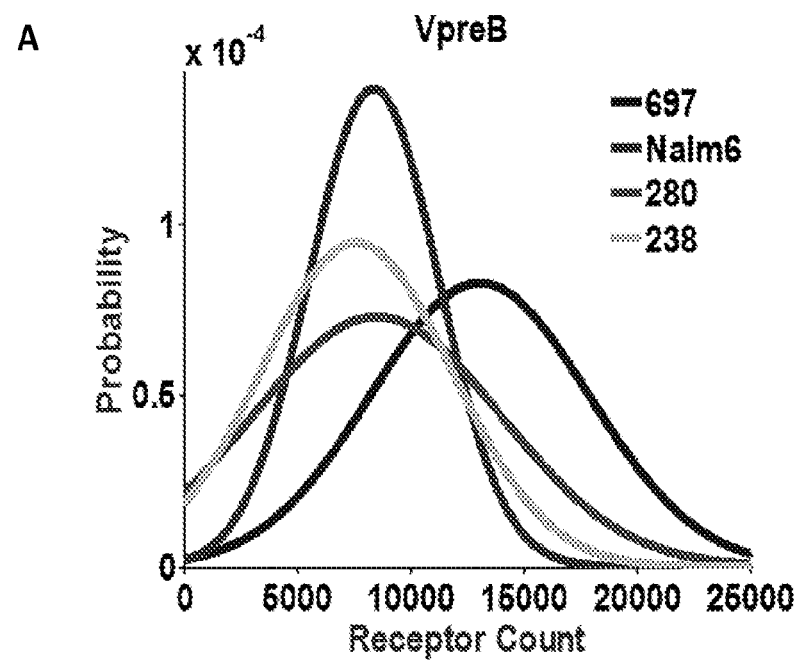
FIG. 13. A) Flow cytometry-based analysis of surface expression for surrogate light chain component VpreB and signaling subunit Igβ/CD79b on 697 and Nalm6 cells, as well as primary cells from two BCP-ALL patients (#238, #280). B) Comparison of pre-BCR diffusion coefficients as derived from ensemble MSD from each 50-second acquisition sequence on both cell lines and primary cells. C) Treatment of 697 cells with inhibitors of lyn (dasatinib) or Syk (Bay-61-3606), but not Jak (tofacitinib) results in a global increase in pre-BCR diffusion relative to tonic signaling. D) An increase in pre-BCR diffusion is observed in patient #280 cells after treatment with anti-VpreB Fabs (5 μM).
Figure 13:
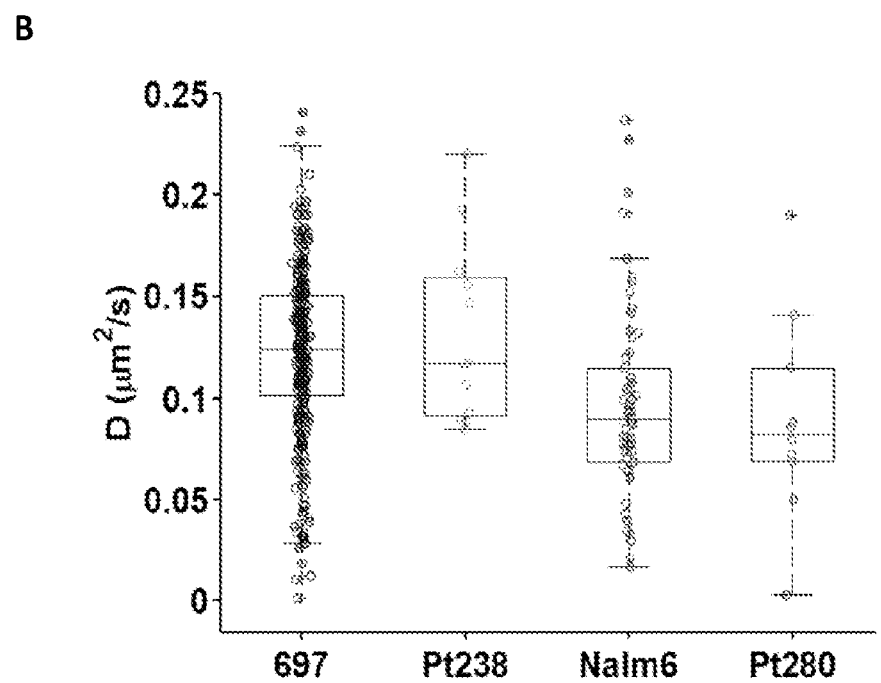
Figure 13:
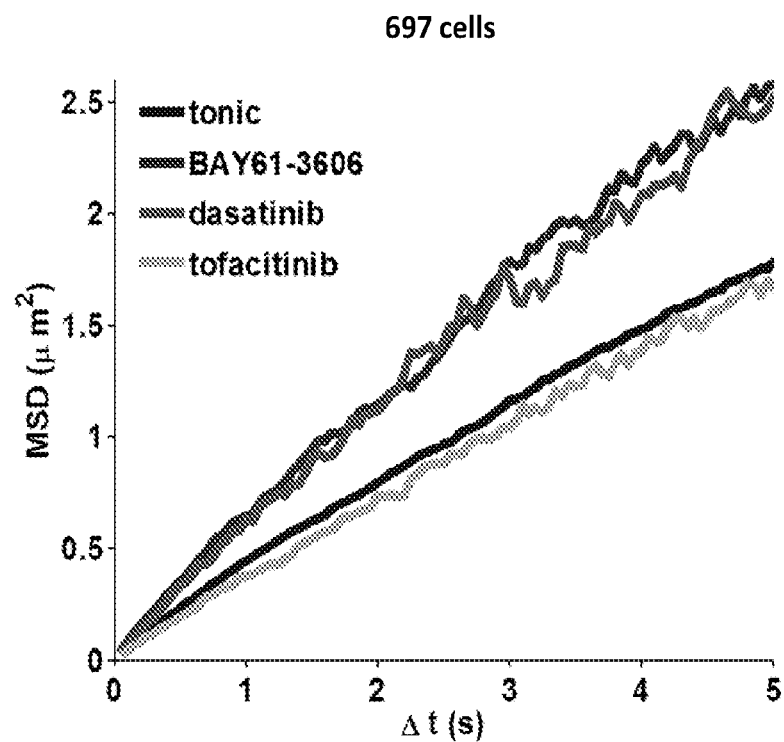
Figure 13:
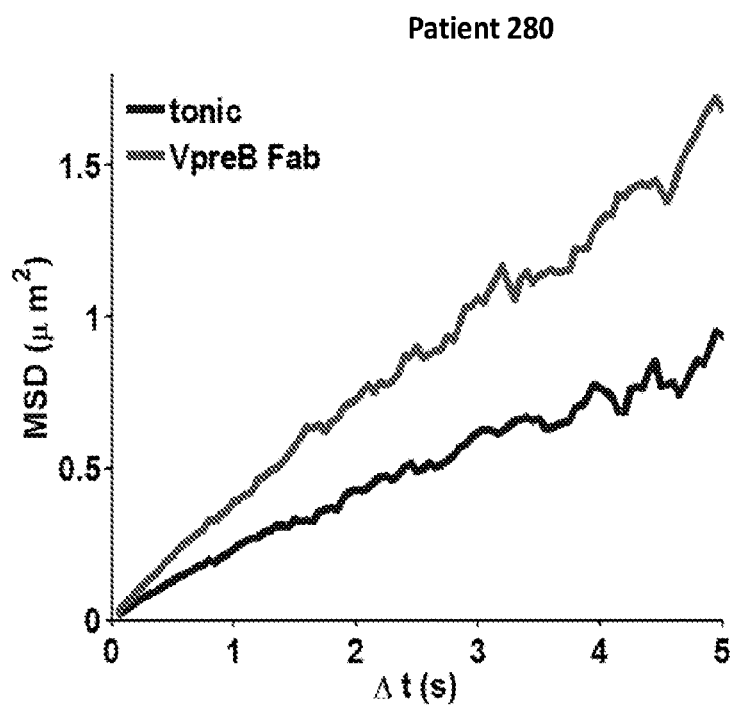

Additional lead candidates for preclinical evaluation can be selected based on specific criteria, including those listed in Table 4.

value. FIG. 13 reports data using cells from two distinct BCP-ALL patient samples (#280, #238) with measurable levels of pre-BCR cell surface expression. To enable repeated measures of primary cells for validation of pre-BCR diffusion and drug sensitivity studies, the patient samples were cryopreserved on the day of acquisition and

TABLE 4

Methods and criteria for selection of lead candidate antibodies

|  | Assay | Selection Criteria |
|---|---|---|
| Protein binding | ELISA binding assay to recombinant h-VpreB and kinetic analysis | Appropriate binding in ELISA and a relevant potency, $K_D < 10^{-9}$M as determined by ELISA |
| Binding to pre-BCR-expressing cells | Flow cytometry (FACS) & microscopy of human pre-BCR expressing cell lines. Nalm-6; RS4; 11, REH | Specific binding to membrane bound human pre-BCR; internalization |
| Binding to primary blast cells | Flow cytometry (FACS) of human primary blasts from patients diagnosed with BCP-ALL | Binding to primary tumor cells from several donors |
| Specific cell killing | Antibody-dependent cell-mediated cytotoxicity & phagosytosis assays (ADCC, ADCP) of cell lines expressing VpreB/I5 (Nalm-6 and 697 cells). Validation of effectors using primary patient material as target cell population. | Effective ADCC and ADCP in vitro against multiple target cell populations of different origins. For example, >40% specific cell death of cell lines and efficacy on primary patient material. Follow up lead candidate(s) in xenograft model |
| Pre-BCR signaling |  | Characterization |
| Reactivity with VpreB from appropriate toxicological species | ELISA and Histology Binding to mouse and cynomolgus (Macaca fascicularis) recombinant VpreB | Reactivity to human VpreB and at least one relevant species usable in toxicology investigations. |
| Domain mapping | Recombinant domains of human VpreB | Identify the domain of VpreB protein to which the MAb binds. Select lead Ab(s) and backups with different selectivity. |

Figure 7:
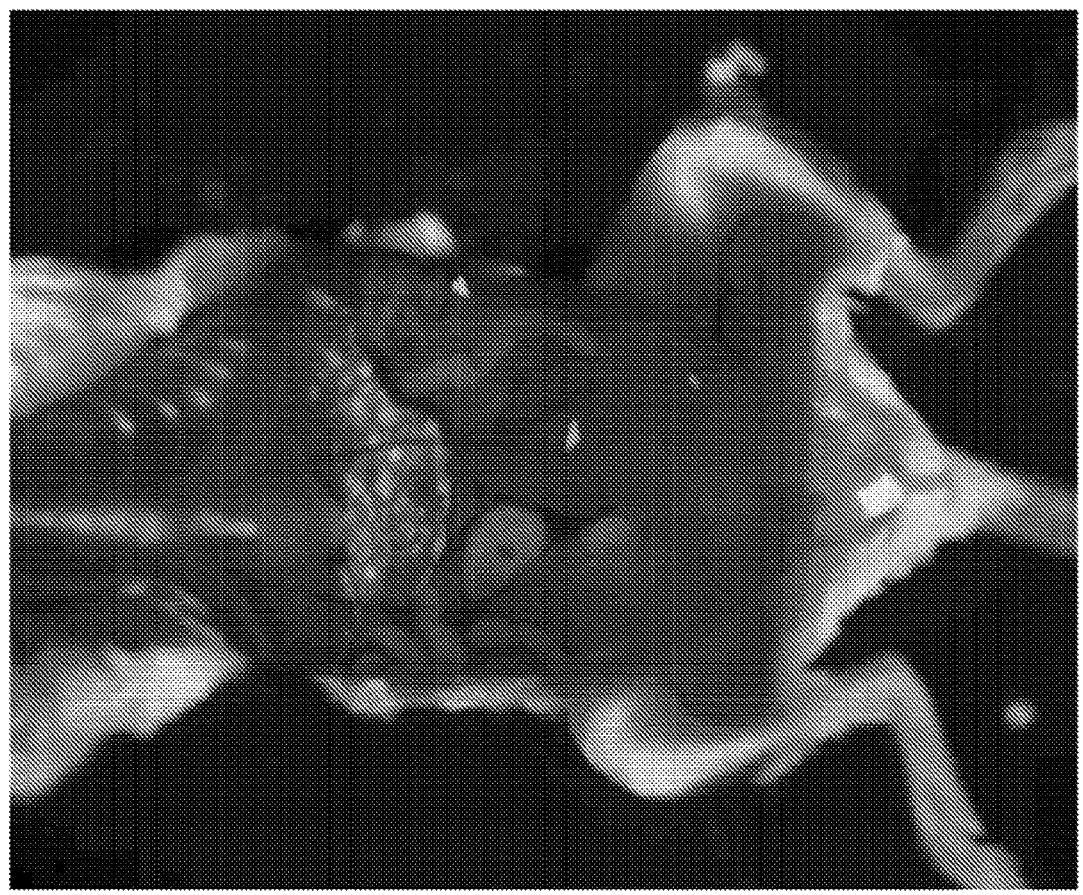
FIG. 7. Preclinical studies of therapeutic antibodies and their derivatives are performed in a xenograft model for BCP-ALL.

Preclinical activity of selected antibodies can be initially tested in vitro and in vivo. Results in FIG. 6A and FIG. 6B show that incubation of BCP-ALL cells with intact anti-VpreB1 antibodies, followed by co-incubation with human NK cells, leads to antibody-dependent cytotoxicity (ADCC). Preclinical studies can also be supported an established human xenograft model where human BCP-ALL cell lines are engrafted into immunocompromised mice. The image shown in FIG. 7 documents the dissemination of GFP-expressing BCP-ALL cells in bone, spleen and liver in SCID or NSG mice. Disease progresses very reliably over a three-week time period after tail vein injection of 697 or Nalm-6 cells; for the latter, blasts also disseminate to brain. One week after engraftment, blocking intact or modified antibodies can be administered over defined dosing schedules for up to two additional weeks, followed by sacrifice of the treated animals and removal of organs.

Patient-derived cells that have been passaged through mice provide a method to expand primary cells for preclinical testing and illustrate the utility of PDX mouse models. Apoptotic cells and alterations in proliferation can be scored in tissue section by IHC staining for annexin and Ki-67. One also can detect and recover fluorescent lymphoblasts from mice. Fluorescent blasts can be assayed by flow for Syk and AKT phosphorylation, cell cycle stage, and apoptosis.

Expression of pre-BCR is reported to be absent in BCR-ABL1+ acute lymphoblastic leukemia, while its expression in other BCP-ALL subsets likely defines those patients for which therapies targeting tonic signaling are of potential then either placed in tissue culture immediately after thawing or passaged through Nod-SCID-γ2-deficient mice.

FIG. 13A shows surface expression of mIgµ for these two patient samples ranges from approximately 4000 to 15,000 copies per cell, with average values of 6000 to 7000. These values are very similar to the levels on Nalm6 cells and about half that of mIgµ expression levels on 697 cells.

The anti-Igβ Fab-QD probes were used for Single Particle Tracking (SPT) tracking to evaluate the diffusion of pre-BCR on untreated primary cells. Results in FIG. 13C show that while the overall diffusion coefficient for pre-BCR on #238 cell membranes is similar to 697 cells, there is essentially no immobile fraction. The spread of observed values, as well as the overall diffusion coefficient for pre-BCR on #280, matches well with diffusion characteristics of pre-BCR on Nalm6 cells. As an extension of the drug profiling reported above, 697 cells were treated with each of the three tyrosine kinase inhibitors in SPT experiments. Treatment of 697 cells with Lyn and Syk inhibitors (dasatinib and Bay-61-3606 respectively) resulted in overall increased mobility for pre-BCR (FIG. 13D), consistent with ITAM phosphorylation creating docking sites for signaling partners that slow receptor diffusion. Incubation of patient #280 cells with either anti-VpreB Fab or dasatinib resulted in notable increase in receptor mobility (FIG. 13E).

Figure 14:
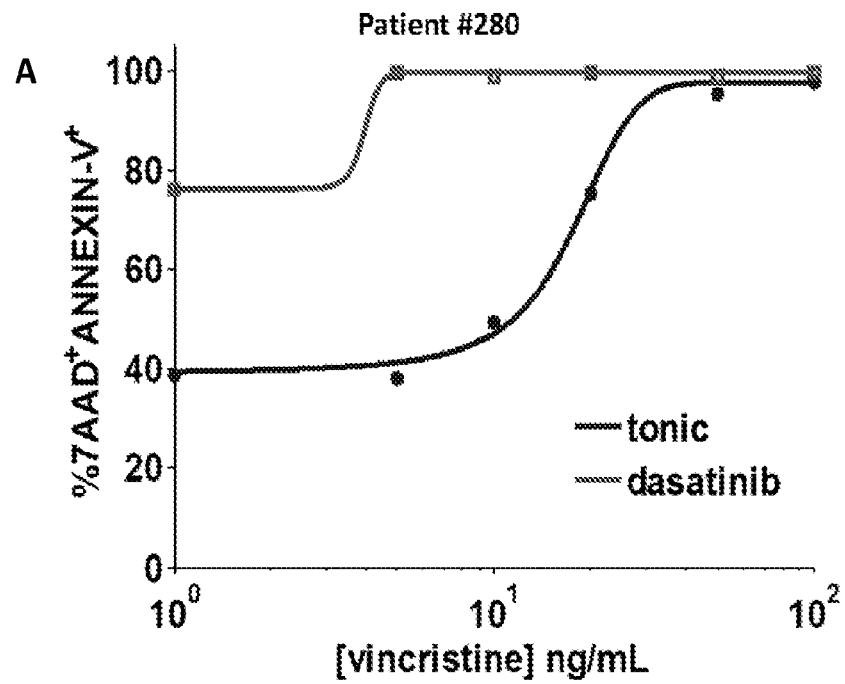
FIG. 14. Data showing that pre-BCR signaling contributes to survival of some BCP-ALL blasts. Data are shown for patient #280. A) Increase in apoptosis (Annexin labeling) and loss of cell viability (7AAD labeling) after prolonged incubation with dasatinib (10 μM) alone or in combination with vincristine over doses of 0.1 ng/ml to 100 ng/ml. B) Increase in apoptosis after 24-hour incubation of #280 patient cells with α-VpreB Fab (5 μM) alone or in combination with low dose vincristine (10 ng/ml). C,D) Treatment of patient #280 cells with α-VpreB Fab, dasatinib or 3AC for 24 hours led to a marked decline in BCL6 levels.
Figure 14:
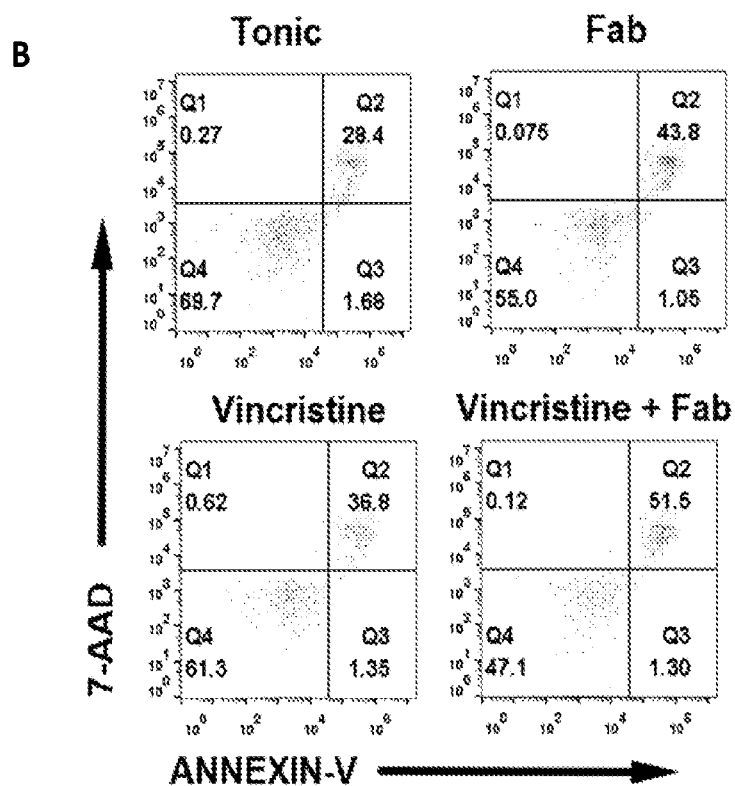
Figure 14:
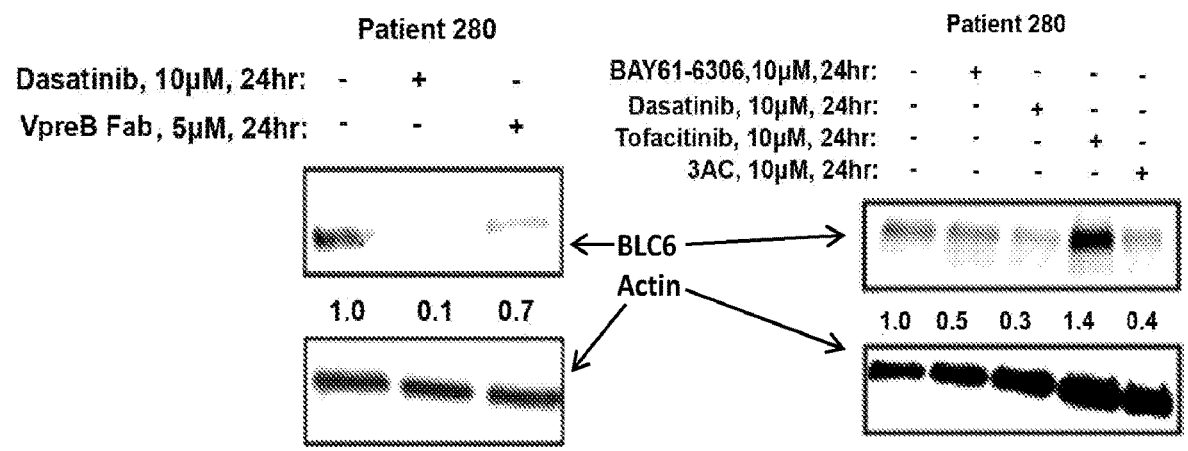

Blockade of pre-BCR homotypic self-association can sensitize patient cells to vincristine. FIG. 14A shows that incubation of cells from patient #280 with anti-VpreB Fabs enhanced apoptosis, whether administered alone or in combination with low dose vincristine. Blasts from patient #280 also were very sensitive to dasatinib as a single agent (80% 7-AAD/Annexin-V positive after 24-hour culture). Longer incubations were not feasible, since cells from this patient were 40% 7-AAD positive when incubated with no drug or in the presence of vincristine up to 5 ng/ml. Taken together, the data demonstrate that agents targeting the pre-BCR or its downstream partners can lead to lymphoblast killing in vitro.

Thus, in one aspect, this disclosure describes a composition that generally includes an antagonist of pre-BCR. As used herein, the term "antagonist" refers to a compound that can combine with a receptor (e.g., pre-BCR) to inhibit a cellular activity of the receptor. An antagonist may be a ligand that directly binds to the receptor. Alternatively, an antagonist may combine with a receptor indirectly by, for example, (a) forming a complex with another molecule that directly binds to the receptor, or (b) otherwise results in the modification of another compound so that the other compound directly binds to the receptor. As used herein, "inhibit" refers to any measurable reduction of cellular activity. The extent of inhibition may be characterized as a percentage of a normal level of activity. Consequently, "inhibit" includes but does not require complete silencing of activity.

In some cases, the antagonist can be an antibody that specifically binds to pre-BCR. As used herein, the term "specifically binds" refers to having a differential or a non-general affinity, to any degree, for a particular target.

As used herein, the term "antibody" refers to any portion of an immunoglobulin capable of specifically binding to a particular target. Thus, in some embodiments, the antibody can be an antibody fragment such as, for example, a monovalent form of the antibody (Fab-Fc) or an intact antibody conjugated to a toxin. Once an antibody is identified, the antibody may be produced by any suitable means including, for example, recombinant techniques, synthetic techniques, expression from a hybridoma, and/or chemical modification of a monoclonal antibody produced by a hybridoma.

In addition to human or humanized antibodies and their derivatives, the Fab binding site of the antibody can be fused in frame to components of the TCR or other ITAM-bearing immunoreceptors, the sequences encoding this "chimeric receptor" inserted into a viral vector, and introduced into T cells isolated from patients for T cell mediate immunotherapy.

The composition described herein may be formulated in a composition along with a pharmaceutically acceptable carrier. As used herein, "carrier" generally includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with a pre-BCR antagonist without causing any undesirable biological effects or interacting in a deleterious manner with any of the other components of the pharmaceutical composition in which it is contained.

A pre-BCR antagonist may be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.). A composition also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing the pre-BCR antagonist into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

A pre-BCR antagonist may be provided in any suitable form including but not limited to a solution, a suspension, an emulsion, nanocarrier or any form of mixture. The composition may be delivered in formulation with any pharmaceutically acceptable excipient, carrier, or vehicle.

The amount of pre-BCR antagonist administered can vary depending on various factors including, but not limited to, the weight, physical condition, and/or age of the subject, and/or the route of administration. Thus, the absolute amount of pre-BCR antagonist included in a given unit dosage form can vary widely, and depends upon factors such as the species, age, weight and physical condition of the subject, as well as the method of administration. Accordingly, it is not practical to set forth generally the amount that constitutes an amount of pre-BCR antagonist effective for all possible applications. Those of ordinary skill in the art, however, can readily determine the appropriate amount with due consideration of such factors.

Generally, the amount of pre-BCR antagonist is an amount effective to ameliorate at least one symptom or clinical sign of BCP-ALL. As used herein, the term "ameliorate" refers to any reduction in the extent, severity, frequency, and/or likelihood of a symptom or clinical sign characteristic of a BCP-ALL. As used herein, "symptom" refers to any subjective evidence of a patient's condition related to BCP-ALL; "sign" or "clinical sign" refers to an objective physical finding relating to BCP-ALL capable of being found by one other than the patient.

In some embodiments, the method can include administering sufficient pre-BCR antagonist as a single agent. Therapeutic antibodies have been administered at doses of from 0.1-20 mg/kg, although in some embodiments the methods may be performed by administering the pre-BCR antagonist in a dose outside this range. Modifications of the antibody, including addition of toxin, alteration of glycosylation status, switching of IgG subclass, or other engineered traits can alter the pharmacokinetics, size, effector function, off-target toxicity and binding characteristics. In some of these embodiments, the method may include combination therapy, either co-administered or in a series with another therapeutic agent.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184. In such embodiments, the method can include administering sufficient pre-BCR antagonist to provide a dose of, for example, from about 0.01 mg/m$^2$ to about 10 mg/m$^2$.

In some embodiments, a pre-BCR antagonist may be administered, for example, from a single dose to multiple doses per week, although in some embodiments the method can be performed by administering a pre-BCR antagonist at a frequency outside this range. In certain embodiments, a pre-BCR antagonist may be administered from about once per month to about five times per week.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the exemplary embodiments described herein. It is to be understood that the particular examples, materials, amounts, and procedures are to be interpreted broadly in accordance with the scope and spirit of the invention as set forth herein.

EXAMPLES

Cell Culture and Treatments

Suspension cultures of BCP-ALL cell lines (697, Nalm6) were grown in RPMI 1640 with phenol red (Sigma-Aldrich, St. Louis, Mo.), with 10% (v/v) HI FBS, 1% Penicillin/Streptomycin (Gibco, Gaithersburg, Md.), and L-Glutamine 2 mM. Patient samples were cultured in IMDM, GlutaMAX medium (Gibco, Gaithersburg, Md.) supplemented with 20% (v/v) HI FBS, 1% penicillin/streptomycin, 1× insulin, transferrin and selenium (Gibco, Gaithersburg, Md.), 1 mM sodium pyruvate (Gibco, Gaithersburg, Md.), and 55 µM 2-Mercaptoethanol (Gibco, Gaithersburg, Md.). Prior to experiments, cells were washed twice with Tyrode's solution (Sigma-Aldrich, St. Louis, Mo.). Unless otherwise stated, cells were pretreated for 10 minutes with Bay-61-3606 (Santa Cruz Biotechnology, Inc., Dallas, Tex.; 1 µM), dasatinib (Santa Cruz Biotechnology, Inc., Dallas, Tex.; 1 µM), tofacitinib (Selleck Chemicals LLC, Houston, Tex.; 1 µM), anti-VpreB Fab (1 µM), 3AC (Echelon Biosciences, Inc., Salt Lake City, Utah), and/or recombinant galectin-1 (PreproTech, Inc., Rocky Hill, N.J.; 10 µM), +/− lactose.

Recombinant Anti-VpreB Antibody Screening and Production

The Contextual Combinatorial Immune Repertoire (Con-CIRT) Synthetic Library (Xu et al., 2008, *PNAS* 105:10756-10761), consisting of 56 billion synthetically constructed human antibodies arrayed in over 100 phage-displayed sub-libraries, was panned against recombinant "surrobodies." Surrobodies consist of functional human IgG1 heavy chain, isolated from an anti-influenza H5N1 hemagglutin antibody, and paired with either surrogate light chain components (VpreB1, λ5) or a chimeric polypeptide that is a product of the fusion of human VpreB1 and λ5 genes. Phage bound to surrobodies coated on 96-well microtiter plate were eluted and amplified for use in subsequent round of panning. After four rounds of phage panning, individual clones from enriched pools were analyzed for specific binding by ELISA assay. Testing for VpreB1 binding specificity was performed on ELISA plates coated with chimeric VpreB1-λ5 polypeptide. Detection was quantified with HRP-conjugated anti-myc antibodies, followed by ELISA-based hit identification. After positive identification, 16-phage-derived clones with an affinity range of 0.85-250 nM were sequenced. Clone 2460B04 was selected for integration into a mammalian expression plasmid, followed by transient transfection of HEK293-F cells for production of recombinant IgG antibodies. Intact IgG was reduced to produce anti-VpreB1 Fab fragments. The reactivity of anti-VpreB1 Fabs against live 697 cells was evaluated by flow cytometry. Results are shown in FIG. 5.

Anti-CD79b IgG Purification

CB3-1 hybridoma cells (generously provided by Dr. Max D. Cooper, Emory University) were grown in RPMI 1640 with phenol red (Sigma-Aldrich, St. Louis, Mo.), with 10% (v/v) HI FBS, 1% Penicillin/Streptomycin (ThermoFisher Scientific, Waltham, Mass.), L-Glutamine 2 mM (Gibco, Gaithersburg, Md.) and 1×β-mercaptoethanol (Gibco, Gaithersburg, Md.). Flask cultures were expanded by culturing for two weeks in 250 ml in RPMI media without FBS, followed by collection of media, clarification by centrifugation at 2000 rpm, and filtration through 0.22 µm vacuum filter. Media was circulated overnight (4° C.) on a protein A/G affinity column and IgG eluted with glycine buffer (pH 2.5-3.0). Eluted 1 ml fractions were neutralized with 1 M TRIS buffer (pH 9.0).

Fab Generation, Biotin Conjugation and Quantum Dot Labeling

Fab-biotin probes were prepared as previously described (Low-Nam et al, 2011, *Nat Struct Mol Biol* 18:1244-1249). IgG derived from CB3-1 hybridoma or anti-IgM (Jackson ImmunoResearch Laboratories, Inc., West Grove, Pa.) was dialyzed into sodium acetate solution, pH 4.5, to prepare for addition to pepsin/agarose (ThermoFisher Scientific, Waltham, Mass.) according to manufacturer's instructions. IgG digestion was carried out for five hours at 37° C. and the eluate dialyzed at 4° C. into 100 mM phosphate, 5 mM EDTA, pH 6.0,) to prepare for 2-Mercaptoethylamin (2-MEA; ThermoFisher Scientific, Waltham, Mass.) reduction of interchain disulfides of F(ab')$_2$. The sample was incubated in 2-MEA (50 mM) for 90 minutes at 37° C. and then dialyzed into storage buffer (100 mM phosphate, 5 mM EDTA, pH 6.5-7.0) for four hours at 4° C., exchanging buffer multiple times. The exposed thiol groups, generated from reduction of interchain disulfides, were selectively conjugated to biotin using the EZ-LINK Maleimide-PEG2-Biotin (ThermoFisher Scientific, Waltham, Mass.) and analyzed via SDS-PAGE. To remove upper molecular weight bands (F(ab')$_2$ and undigested IgG), digested fragments recovered at room temperature by FPLC size-exclusion chromatography using Superdex 75 10/300 column (GE Healthcare Life Sciences, Marlborough, Mass.) under isocratic conditions with phosphate buffered saline at 0.5 ml/min flow rate. Residual intact of Fc fragments were removed by batch processing with protein A/G agarose beads (ThermoFisher Scientific, Waltham, Mass.). The biotin:Fab molar ratio was determined by FLUOREPORTER biotective green reagent (ThermoFisher Scientific, Waltham, Mass.). Anti-CD79b Fab-Biotin or Anti-IgM Fab-Biotin were mixed at 1:1 stoichiometry with Qdot655 or Qdot585-streptavidin in PBS+1% (w/v) BSA to generate stock solutions.

QD Labeling of Live Cells

LAB-TEK imaging chambers (ThermoFisher Scientific, Waltham, Mass.) were coated with poly-1-lysine hydrobromide (Sigma-Aldrich, St. Louis, Mo.) at 1 mg/ml in sterile water for 20 minutes at room temperature, followed by three washes. BCP-ALL cells were serum-starved in RPMI 1640 without FBS for two hours prior to being added to coated wells and incubated for 15 minutes at 37° C. QD-Fab-CD79b or QD-Fab-IgM were added at 100 pM in Tyrodes's solution (Sigma-Aldrich, St. Louis, Mo.) with 0.1% (w/v) BSA and 20 mM glucose for 10-15 minutes at 37° C.

Single Particle Tracking and Analysis

All corresponding GPU single particle tracking and track elongation, squared displacement, mean square displacement, correlated motion, fiducial data acquisition and image registration and three-state hidden Markov Model used in this study have been described in detail previously (Low-Nam et al, 2011, *Nat Struct Mol Biol* 18:1244-1249).

Galectin-1 Cloning, Expression and Purification

MGC Human Galectin-1 coding cDNA (LGALS1, accession# BC001693) was PCR amplified using CACC forward primer (FWD: 5'-CAC CAT GGC TTG TGG TCT GG-3'; SEQ ID NO:4) and reverse primer (REV: 5'-TCA GTC AAA GGC CAC ACA TTT GAT CT-3'; SEQ ID NO:5). Amplified product was cloned into pET101 using a pET101 directional TOPO expression kit (ThermoFisher Scientific, Waltham, Mass.) and cloned product was transformed into ONE SHOT TOP10 *E. coli* (ThermoFisher Scientific, Waltham, Mass.) by heat-shock. Cells were grown overnight on ampicillin. Resistant cultures were selected and DNA isolated. BL21 STAR ONE SHOT cells (ThermoFisher Scientific, Waltham, Mass.) were transformed with the pET101 vector with LGALS1 by heat-shock, brief outgrowth in SOC medium (ThermoFisher Scientific, Waltham, Mass.) followed by transformation to 10 mL LB containing ampicillin. Cultures were grown overnight at 37° C. while shaking. On the following day, 50 mL of LB with ampicillin was inoculated with 1 mL of overnight culture. The culture was grown at 37° C. with shaking (225-250 rpm) for two to three hours. IPTG (1 mM) was added for three to four hours to induce expression. After IPTG induction, cells were harvested by centrifugation (3000×g for 10 minutes at 4° C.). Cells were purified by α-lactose/agarose (Sigma-Aldrich, St. Louis, Mo.) as detailed previously (Carlow et al., 2003, *J Immunol* 171:5100-5106).

Western Blotting

After stated incubation +/− inhibitors or crosslinking agents, cells were washed with ice-cold PBS and held for 15 minutes on ice in Tris-based lysis buffer, with 1% NP-40 and protease and phosphatase inhibitors (ThermoFisher Scientific, Waltham, Mass.). For effects of inhibitors on BCL6 expression, treatments were carried out for 24 hours. Lysates were clarified by centrifugation at 14,000×g for 10 minutes at 4° C., then added to Laemmli's Reducing buffer. Proteins were separated on SDS-polyacrylamide and transferred to nitrocellulose membranes. After blocking with TBST (Sigma-Aldrich, St. Louis, Mo.) with 5% BSA (Sigma-Aldrich, St. Louis, Mo.), blots were probed with antibodies specific to pCD79a (Tyr 182) (Cell Signaling Technology, Inc., Danvers, Mass.), pSyk (Tyr348) (Novus Biologicals LLC, Littleton, Colo.), pSyk (Tyr 352) (Cell Signaling Technology, Inc., Danvers, Mass.) or BCL6 (Santa Cruz Biotechnology, Inc., Dallas, Tex.). Antibodies to β-Actin (Sigma-Aldrich, St. Louis, Mo.) were used as loading controls.

Pervanadate Treatment

BCP-ALL cells were treated with pervanadate solution as previously described (Imbert et al., 1994, *Biochem J* 297 (Pt 1):163-173; Smrz et al., 2008, *J Biol Chem* 283:10904-10918). Data in FIG. 8 are reported using a linear range normalization from 0 to 1.0, whereby tonic without pervanadate treatment response was set to 0 and tonic pervanadate treatment was set to 1.0:

$$Normalized\ Value = \frac{(Response - (MinTonResponse))}{MaxTonResponse - MinTonResponse}$$

Chemosensitization

To establish an effective dose range for potential synergy of targeted inhibitors with vincristine, 697 cells were incubated for three days at 37° C. with a range of 0.1-100.0 ng/mL vincristine (Sigma-Aldrich, St. Louis, Mo.); 50,000 cells were used per condition. Curves were fit using sigmoidal dose-response curve using MATLAB curve fitting toolbox (The MathWorks, Inc., Natick, Mass.).

$$\%\ Response = \min(\%\ response) + \frac{(\max(\%\ response) - \min(\%\ response))}{1 + 10^{(LogEC_{50} - [vincristine]) * HillSlope}}$$

Flow Cytometry Assays

Leukemia cell apoptosis was measured based upon binding to Annexin-V-FITC (BioLegend, Inc., San Diego, Calif.) and loss of cell viability measured by 7-AAD labeling (BioLegend, Inc., San Diego, Calif.), according to manufacturer's procedures. For receptor-binding experiments, cells were incubated under saturating conditions for 1.5 hours on ice in PBS with anti-CD79b-APC antibody (BioLegend, Inc., San Diego, Calif.) or anti-VpreB-PE antibody (BioLegend, Inc., San Diego, Calif.). Flow results were calibrated using QUANTUM SIMPLY CELLULAR (Bangs Laboratories, Inc., Fishers, Ind.) beads with anti-mouse Fc antibody according to manufacturer's instruction. Dissociation constants were estimated with nonlinear regression analysis under KD controlled conditions as described (Drake, A. W., and S. L. Klakamp, 2007, *J Immunol Methods* 318:147-152). All flow cytometry data collection was conducted on the HYPERCYT platform (IntelliCyt Corp., Albuquerque, N. Mex.; Edwards et al., 2009, *Methods Mol Biol* 486:151-165) and analyzed with the FLOWJO Software Suite (FlowJo, LLC, Ashland, Oreg.).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

| Sequence Listing Free Text |
|---|
| SEQ ID NO: 1<br>UniProt accession no.: P12018, Signal Peptide 1-19<br>MSWAPVLLMLFVYCTGCGP |
| SEQ ID NO: 2<br>UniProt accession no.: P12018\|20-145, Immuno-globulin iota chain<br>QPVLHQPPAMSSALGTTIRLTCTLRNDHDIGVYSVYWYQQRPGHPPRFLL<br>RYFSQSDKSQGPQVPPRFSGSKDVARNRGYLSISELQPEDEAMYYCAMGA<br>RSSEKEEREREWEEEMEPTAARTRVP |
| SEQ ID NO: 3<br>UniProt accession no.: P12018, Signal Peptide + Immunoglobulin iota chain<br>MSWAPVLLMLFVYCTGCGPQPVLHQPPAMSSALGTTIRLTCTLRNDHDIG<br>VYSVYWYQQRPGHPPRFLLRYFSQSDKSQGPQVPPRFSGSKDVARNRGYL<br>SISELQPEDEAMYYCAMGARSSEKEEREREWEEEMEPTAARTRVP |
| SEQ ID NO: 4<br>5'-CACCATGGCTTGTGGTCTGG-3' |
| SEQ ID NO: 5<br>5'-TCAGTCAAAGGCCACACATTTGATCT-3' |

What is claimed is:

1. A method comprising:
   administering to a subject having B cell precursor acute lymphoblastic leukemia (BCP-ALL) a therapeutic composition in an amount effective to ameliorate at least one symptom or clinical sign of BCP-ALL, the therapeutic composition comprising an antibody comprising the amino acid sequences of SEQ ID NO:7, SEQ ID NO:8, SEQ ID NO:9, SEQ ID NO:11, SEQ ID NO:12, and SEQ ID NO:13.

2. The method of claim 1, wherein the antibody is humanized.

3. The method of claim 1, wherein the therapeutic composition further comprises a toxin conjugated to the antibody.

4. The method of claim 1, wherein the antibody light chain comprises the amino acid sequences of SEQ ID NO:7, SEQ ID NO:8, and SEQ ID NO:9.

5. The method of claim 1, wherein the antibody heavy chain comprises the amino acid sequences of SEQ ID NO:11, SEQ ID NO:12, and SEQ ID NO:13.

6. The method of claim 4, wherein the antibody light chain comprises SEQ ID NO:6.

7. The method of claim 5, wherein the antibody heavy chain comprises SEQ ID NO:10.

* * * * *

UNITED STATES PATENT AND TRADEMARK OFFICE
CERTIFICATE OF CORRECTION

PATENT NO. : 10,988,533 B2  
APPLICATION NO. : 15/548871  
DATED : April 27, 2021  
INVENTOR(S) : Wilson et al.

Page 1 of 1

It is certified that error appears in the above-identified patent and that said Letters Patent is hereby corrected as shown below:

On the Title Page

Item (71), Applicants, 'STC.UNM' should read -UNM Rainforest Innovations-

Item (71), Applicants, remove 'Bridget S. Wilson, Albuquerque, NM (US)'

Item (71), Applicants, remove 'Stuart S. Winter, Albuquerque, NM (US)'

Item (71), Applicants, remove 'Michael Frank Erasmus, Santa Fe, NM (US)'

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*